United States Patent
Bennicelli et al.

(10) Patent No.: US 10,857,240 B2
(45) Date of Patent: Dec. 8, 2020

(54) METHODS AND COMPOSITIONS FOR TREATMENT OF OCULAR DISORDERS AND BLINDING DISEASES

(71) Applicant: The Trustees of the University of Pennsylvania, Philadelphia, PA (US)

(72) Inventors: Jeannette Bennicelli, Philadelphia, PA (US); Jean Bennett, Bryn Mawr, PA (US); Junwei Sun, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 90 days.

(21) Appl. No.: 16/066,970

(22) PCT Filed: Jan. 5, 2017

(86) PCT No.: PCT/US2017/012277
§ 371 (c)(1),
(2) Date: Jun. 28, 2018

(87) PCT Pub. No.: WO2017/120294
PCT Pub. Date: Jul. 13, 2017

(65) Prior Publication Data
US 2018/0369415 A1      Dec. 27, 2018

Related U.S. Application Data

(60) Provisional application No. 62/275,006, filed on Jan. 5, 2016.

(51) Int. Cl.
*C12N 15/86*       (2006.01)
*A61K 48/00*       (2006.01)
*C12N 9/02*        (2006.01)
*A61P 27/02*       (2006.01)
*A61K 38/44*       (2006.01)

(52) U.S. Cl.
CPC ............ *A61K 48/005* (2013.01); *A61K 38/44* (2013.01); *A61K 48/00* (2013.01); *A61K 48/0075* (2013.01); *A61P 27/02* (2018.01); *C12N 9/0036* (2013.01); *C12N 9/0051* (2013.01); *C12N 15/86* (2013.01); *C12N 2750/14143* (2013.01); *C12N 2800/22* (2013.01); *C12N 2830/001* (2013.01)

(58) Field of Classification Search
CPC ..................................................... C12N 15/86
See application file for complete search history.

(56) References Cited

U.S. PATENT DOCUMENTS

| 7,795,387 | B2 | 9/2010 | Leveillard et al. |
| 8,114,849 | B2 | 2/2012 | Leveillard et al. |
| 8,394,756 | B2 | 3/2013 | Leveillard et al. |
| 8,518,695 | B2 | 8/2013 | Leveillard et al. |
| 8,957,043 | B2 | 2/2015 | Leveillard et al. |
| 2009/0062188 | A1 | 3/2009 | Leveillard et al. |
| 2014/0087444 | A1 | 3/2014 | Bennett et al. |
| 2014/0107186 | A1 | 4/2014 | Garcia et al. |

FOREIGN PATENT DOCUMENTS

| WO | WO 2013/063383 A2 | 5/2013 |
| WO | WO 2013/093029 A2 | 6/2013 |
| WO | WO 2016/185037 A1 | 11/2016 |
| WO | WO 2016/185242 A1 | 11/2016 |

OTHER PUBLICATIONS

NCBI printout 2019—3 pages (Year: 2019).*
Fath et al. (2011, PLOS One, vol. 6(3), pp. 1-14). (Year: 2011).*
Bennicelli, J et al, Reversal of Blindness in Animal Models of Leber Congenital Amaurosis Using Optimized AAV2-mediated Gene Transfer, Mol. Ther., Mar. 2008, 16(3):458-465.
Byrne et al, "Viral-mediated RdCVF and RdCVFL expression protects cone and rod photoreceptors in retinal degeneration", J. Clin. Invest., Jan. 2015, 125(1):105-116.
Caporale N. et al, LiGluR Restores Visual Responses in Rodent Models of Inherited Blindness, Mol. Therapy, Jul. 2011, 19(7):1212-1219.
Jaillard et al. "Nxnl2 splicing results in dual functions in neuronal cell survival and maintenance of cell integrity." Human Mol. Genet., Feb. 2012, 21(10):2298-2311.
Kotin, RM, Apr. 2011 Large-scale recombinant adeno-associated virus production., Hu. Mol. Genet, 20(1): R1-R6.
Maguire, AM et al., Oct. 2009 Age-dependent effects of RPE65 gene therapy for Leber's congenital amaurosis: a phase 1 dose-escalation trial. Lancet, DOI:10.1016/S0140-6736(09)61836-5.
Smith, RH et al, A Simplified Baculovirus-AAV Expression Vector System Coupled With One-step Affinity Purification Yields High-titer rAAV Stocks From Insect Cells, Mol. Ther., Jun. 2009, 17(11): 1889-1896.

(Continued)

Primary Examiner — Thaian N. Ton
Assistant Examiner — David A. Montanari
(74) Attorney, Agent, or Firm — Howson & Howson LLP; Colleen M. Schaller

(57) ABSTRACT

Codon optimized nucleic acid sequences for the long form and short form of RdCVF are provided, as well as recombinant viral vectors, such as AAV, expression cassettes, proviral plasmids or other plasmids containing the codon optimized sequences. Recombinant vectors are provided that express the codon optimized RdCVFL and RdCVF individually, or express two copies of a codon optimized RdCVF or RdCVFL nucleic acid sequence, or both RdCVFL and RdCVF in a single vector or virus. Compositions containing these codon optimized sequences are useful in methods for treating, retarding or halting certain blinding diseases resulting from the absence or inappropriate expression of RdCVF and RdCVFL.

9 Claims, 10 Drawing Sheets
Specification includes a Sequence Listing.

(56) References Cited

OTHER PUBLICATIONS

International Search Report dated Mar. 13, 2017 in corresponding International Patent Application PCT/US2017/012277, filed Jan. 5, 2017.
Written Opinion dated Mar. 13, 2017 in corresponding International Patent Application PCT/US2017/012277, filed Jan. 5, 2017.

* cited by examiner

FIG. 1 (SEQ ID NO: 1)

*ggccatacaggccgccaccatg*GCCTCACTGTTCTCCGGGCGCATCCTCATCCGAA
ACAACAGCGATCAGGACGAATTGGACACCGAGGCTGAAGTCTCCCGCCGGCTGGAA
AACAGGCTCGTGCTCCTGTTCTTCGGTGCCGGAGCGTGCCCGCAGTGCCAAGCCTT
CGTCCCAATTCTTAAGGACTTCTTTGTGCGCCTCACTGATGAGTTTTACGTGCTCC
GGGCAGCGCAGCTGGCCTTGGTGTATGTGTCGCAAGATTCCACTGAGGAACAACAG
GACCTGTTCCTGAAAGACATGCCTAAGAAGTGGCTTTTCCTGCCCTTCGAGGACGA
CCTGAGAAGGGACCTGGGACGCCAGTTCAGCGTGGAACGGCTGCCGGCCGTCGTGG
TGCTGAAGCCCGACGGGGACGTGCTTACCCGGGATGGCGCTGACGAAATCCAGAGG
CTGGGCACCGCCTGTTTCGCAAATTGGCAGGAGGCCGCCGAAGTGCTCGACCGGAA
CTTCCAGCTGCCCGAGGATCTGGAGGACCAGGAACCTCGGTCCCTGACCGAGTGCC
TCAGACGCCACAAGTACCGCGTGGAAAAGGCCGCGAGAGGAGGACGGGACCCGGGT
GGCGGGGGAGGCGAAGAGGCGGAGCCGGTGGCCTGTTC*tgatagatct*

FIG. 2  (SEQ ID NO: 2)

*gcggccgccaccatg*GCCAGCCTCTTCTCCGGACGCATCCTGATTCGCAACAATTC
CGACCAAGACGAACTGGATACCGAGGCCGAAGTCTCGCGGAGATTGGAGAACAGGC
TTGTGCTGCTGTTCTTTGGCGCGGGAGCGTGTCCTCAGTGCCAGGCTTTCGTGCCA
ATCCTGAAGGATTTCTTCGTGCGGCTGACTGACGAATTCTACGTCCTCCGGGCCGC
CCAGCTGGCACTGGTGTACGTGTCCCAAGACTCAACCGAGGAACAGCAGGATCTGT
TCCTCAAGGACATGCCCAAAAAGTGGCTGTTCCTGCCGTTTGAGGACGACTTGCGG
CGC*tagtgatca*

FIG. 3

```
Opt RdCVF   ATGGCCTCACTGTTCTCCGGGGCATCCCTTCATCCGAAACAACAGCGATCAGGACGAATTG
            |||||||||  ||||| || ||  ||||||  ||||||||  ||||||| |||||| |||
Native      ATGGCCTCCCTGTTCTCTGGCCGCATCCCTGATCCGCAACAATAGCGACCAGGACGAGCTG Opt RdCVF   GACACCGAGGCTGAAGTCTCCCCGGCTGGAAAACAGGCTCGTGCTCCTGTTCTTCGGT
            ||  |  ||||||||||  ||  ||||||||| ||||| |||||||||||||| |||
Native      GATACGGAGGCTGAGGTCAGTCCCGCAGGTGAAAACCGGCTGGAGAACCGGCTGCTGTTCTTTGGT Opt RdCVF   GCCGGGAGCCGTTGTGCCCCGCAGTGCCAAGCCTTCGTCCCAATTCTTAAGGACTTCTTTGTGCGC
            || ||||||| |||||||| ||||||||||||||| ||||| |||||| |||||||||| || |
Native      GCTGGGGGCTTGTCCACAGTGCCCAGGCCTTCGTGCCCATCCTCAAGGACTTCTTCGTGCGG Opt RdCVF   CTCACTGATGAGTTTTTACGTGCTCCGGGCAGCTGGCCTTGGTGTATGTGTCGCAA
            ||||| ||||||||| || ||| || |||||||||||| |||||| ||||| ||
Native      CTCACAGATGAGTTCTATGTACTGCGGGCGGCTCAGCTGGCCCTGGTGTACGTGTCCCAG
```

FIG. 3 (continued)

```
Opt RdCVF  GATTCCACTGAGGAACAACAGGACCTGTTCCTGAAAGACATGCCTAAGAAGTGGCTTTTC
           |||||||||||||||||  |||||||||||||||||||||||||  ||||| ||||||||
Native     GACTCCACGGAGGAGCAGCAGGACCTGTTCCTCAAGGACATGCCAAAGAAATGGCTTTTC Opt RdCVF  CTGCCCTTCGAGGACGACCTGAGAAGGGACCTGGGACGCCAGTTCAGCGTGGAACGGCTG
           |||||||| ||||| |||||  |||| ||||||||| ||||||||| ||| |||||||||
Native     CTGCCCTTTGAGGATGATCTGAGGAGGGACCTCGGCGCCAGTTCTCAGTGGAGCGCCTG Opt RdCVF  CCGGCCGTCGTGGTGCTGAAGCCCGACGTGCTTACCCGGGACGTGCTGACGGAA
           |||| |||||||||||||||||||| |||||| || ||| |||||||||||||||||||
Native     CCGGGCGTCGTGGTGCTCAAGCCGGACGTGCTGCACTCGCCGACGGCGCCGACGAG Opt RdCVF  ATCCAGAGGCTGGGCCACCGCCTGTTTCGCAAATTGGCAGGAGGCCGCGAAGTGCTCGAC
           ||||||||||||||  |||||||||| || |||| ||||||||| || |||||| ||||
Native     ATCCAGCGCCTGGGCCACCGCCTGCTTCGCCAACTGGCAGGGGCCGAGGTGCTGGAC Opt RdCVF  CGGAACTTCCAGCTGCCCGAGGATCTGGAGGACCAGGAACCTCGGTCCCTGACCGAGTGC
           || |||||||||||||||| |||| ||||||||||||| |||| ||||| ||||||||
Native     CGCAACTTCCAGCTGCCCAGAGGACCTGGAGGACCAGGAGCCACGAGCCTCACCGAGTGC
```

FIG. 3 (continued)

```
Opt RdCVF   CTCAGACGCCACAAGTACCGCGTGGAAAAGGCCGCGAGAGGAGGACCCGGGTGGC
            ||  ||||||||||||||||||||||||||||||  ||| |||| || || ||
Native      CTGCGCCGCCACAAGTACCGCGTGGAAAAGGCCGGGCGAGGCGCGACCCCGGGGA Opt RdCVF   GGGGGAGGCGAAGAGGGCCGGAGCCGGTGGCCCTGTTC
            ||||| ||  |||||||||  ||||||| || ||||||
Native      GGGGGTGGGGAGGAGGAGGGCCGGGGGCTGGGGCTGTTC
```

FIG. 4

```
Opt RdCVF  ATGGCCAGCCCTCTTCTCCGGACGGCATCCTGATTCGCAACAATTCCGACCAAGACGAACTG
           ||||||| ||  |||  || ||  ||  ||||| || ||||||| ||||  ||||||| ||
Native     ATGGCCTCCCCTGTTCTCTGGCCGCATCCTGATCCCGCAACATAGCGACCAGGACGAGCTG Opt RdCVF  GATACCGGAGGCCGAAGTCTCGCGGAGATTGGAGAACAGGCTTGTGCTGTTCTTTGGC
           |||| |||||||   ||||| |   || |||||||  |||| ||||| ||||| |||
Native     GATACGGAGGCTGAGGTCAGTGCGCAGGCTGAGAACCGGCTGGTGCTGTTCTTTGGT Opt RdCVF  GCGGGAGCGTGTCCTCAGTGCCAGGCTTTCGTGCCAATCCTGAAGGATTTCTTCGTGCGG
           |   ||||| ||||||||||||||| |||||||||  |||| ||||  || |||||||
Native     GCTGGGGCTTGTCCACAGTGCCAGGCCTTCGTGCCCATCCTCAAGGACTTCTTCGTGCGG Opt RdCVF  CTGACTGACGAATTCTACGTGTCCCTCCCGGGCCGGGCCCAGCTGGCTGTGTACGTGTCCCAA
           ||  | ||  |||| ||||||||||     |||  |||  ||||| ||||||||||||| |
Native     CTCACAGATGAGTTCTATGTGTCCCTCGGGGCGGCTCAGCTGGCCCTGGTGTACGTGTCCCAG
```

FIG. 4 (continued)

```
Opt RdCVF   GACTCAACCGAGGAACAGCAGGATCTGTTCCCTCAAGGACATGCCCAAAAAGTGGCTGTTC
            |||||| || |||| ||||| |||||||||||||||||||||||||||| || ||||| ||| |||
Native      GACTCCACGGAGGAGCAGCAGGACCTGTTCCCTCAAGGACATGCCAAAGAAATGGCTTTTC Opt RdCVF   CTGCCGTTTGAGGACGACTTGCGGCGC
            ||||| ||||||| |||| || || |||
Native      CTGCCCTTTGAGGATGATCTGAGGAGG
```

METHODS AND COMPOSITIONS FOR TREATMENT OF OCULAR DISORDERS AND BLINDING DISEASES

CROSS-REFERENCE TO RELATED APPLICATIONS

This application is a national stage of International Patent Application No. PCT/US2017/012277, filed Jan. 5, 2017, which claims the benefit of the priority of U.S. Provisional Patent Application No. 62/275,006, filed Jan. 5, 2016, which applications are incorporated herein by reference.

INCORPORATION-BY-REFERENCE OF MATERIAL SUBMITTED IN ELECTRONIC FORM

Applicant hereby incorporates by reference the Sequence Listing material filed in electronic form herewith. This file is labeled "15-7572PCT_SEQ_List_ST25.txt" and dated Jan. 4, 2017.

BACKGROUND OF THE INVENTION

Rod-cone dystrophies, such as retinitis pigmentosa (RP), are genetically heterogeneous retinal degenerative diseases characterized by the progressive death of rod photoreceptors, followed by the consecutive loss of cones. RP patients initially present with loss of vision under dim-light conditions as a result of rod dysfunction, with relative preservation of macular cone-mediated vision. As the disease progresses, however, the primary loss of rods is followed by cone degeneration and a deficit in corresponding cone-mediated vision. Retention of cone-mediated sight in RP patients would lead to a significant improvement in their quality of life.

A variety of methods for treatment of such diseases have involved a protein, termed RdCVF, which is differentially transcribed and expressed in subjects suffering from retinal dystrophies, including age-related macular degeneration. The long (RdCVFL) and short (RdCVF) forms produced by alternative splicing of the NXNL1 gene have been identified in humans and other mammals. See, e.g., US Patent Application Publication No. US2009/0062188; Byrne et al "Viral-mediated RdCVF and RdCVFL expression protects cone and rod photoreceptors in retinal degeneration", January 2015, J. Clin. Invest., 125(1):105-116.

No currently approved treatment for retinal degenerations exists other than one treatment which involves oral administration of high dose vitamin A. That treatment, however, is controversial and now that we know more about the retinoid cycle in retinal degenerations, is, in fact, likely to worsen retinal degeneration in many genetic forms of retinal disease.

A continuing need in the art therefore exists for new and effective tools to facilitate treatment of ocular diseases such as retinal degenerations, RP, macular degeneration, and other rod-cone dystrophies and retinal degenerative diseases.

SUMMARY OF THE INVENTION

In one aspect, a codon optimized cDNA sequence SEQ ID NO: 1 encoding human RdCVFL long form or a codon optimized cDNA sequence SEQ ID NO: 2 encoding RdCVF short form is provided.

In another aspect an expression cassette comprises a codon optimized nucleic acid sequence SEQ ID NO: 1 that encodes RdCVFL or a codon optimized nucleic acid sequence SEQ ID NO: 2 that encodes RdCVF, or both a codon optimized nucleic acid sequence SEQ ID NO: 2 that encodes RdCVF and a codon optimized nucleic acid sequence SEQ ID NO: 1 that encodes RdCVFL, or two copies of a codon optimized nucleic acid sequence SEQ ID NO: 2 that encodes RdCVF, or two copies of a codon optimized nucleic acid sequence SEQ ID NO: 1 that encodes RdCVFL. In still other embodiments, the expression cassette is positioned between 5' and 3' AAV ITR sequences, then referred to as an rAAV genome.

In another aspect, a vector is provided that contains one or more of the expression cassettes described herein and host cells containing the vectors or expression cassettes are provided.

In another aspect, a proviral plasmid comprises sequences encoding an AAV capsid and an recombinant AAV genome that comprises AAV inverted terminal repeat sequences and an expression cassette comprising the codon optimized nucleic acid sequence(s) that encodes RdCVFL, RdCVF-S, both RdCVFL and RdCVF, two copies of RdCVF, or two copies of RdCVFL, and expression control sequences that direct expression of the encoded protein(s) in a host cell. In certain embodiments, the AAV genome is modular.

In another embodiment, a recombinant adeno-associated virus (AAV) comprises an AAV capsid and an recombinant AAV genome that comprises AAV inverted terminal repeat sequences and an expression cassette comprising a codon optimized nucleic acid sequence that encodes RdCVFL, RdCVF, both RdCVF and RdCVFL, or two copies of RdCVF or two copies of RdCVFL, and expression control sequences that direct expression of the encoded protein(s) in a host cell.

In yet a further aspect a pharmaceutical composition comprises a pharmaceutically acceptable carrier, diluent, excipient and/or adjuvant and the nucleic acid sequence, a plasmid, a vector, or a viral vector, such as the rAAV, described specifically herein.

In another aspect, a method for treating, retarding or halting progression of blindness in a mammalian subject comprises administering the compositions described herein containing a codon optimized cDNA sequence encoding human RdCVFL long form or RdCVF short form, or both forms of RdCVF or multiple copies of the short or long form.

In yet a further aspect, a method of generating a recombinant rAAV comprises culturing a packaging cell carrying a plasmid or proviral plasmid containing the codon optimized cDNA sequence encoding human RdCVFL long form or RdCVF short form, or both forms of RdCVF or multiple copies of the short or long form, in the presence of sufficient viral sequences to permit packaging of the AAV viral genome into an infectious AAV envelope or capsid.

Still other aspects and advantages of these compositions and methods are described further in the following detailed description of the preferred embodiments thereof.

BRIEF DESCRIPTION OF THE DRAWINGS

FIG. 1 (SEQ ID NO: 1) is a human codon optimized DNA sequence encoding RdCVFL with N-terminal SfiI and Kozak and C-terminal BglII restrictions sites added for cloning. Nucleotides 23-655 of SEQ ID NO: 1 represent the sequence of codon optimized RdCVFL. The restriction sites are represented by italicized and lower case lettering at nucleotides 1-22 and 656-665 of SEQ ID NO: 1.

FIG. 2 (SEQ ID NO: 2) is a human codon optimized DNA sequence encoding RdCVF with N-terminal NotI and Kozak and C-terminal MI restrictions sites added for cloning. Nucleotides 16-339 of SEQ ID NO: 2 represent the sequence of codon optimized RdCVF (short form). The restriction sites are represented by italicized and lower case lettering at nucleotides 1-15 and 340-348 of SEQ ID NO: 2.

FIG. 3 is the alignment of the long form of optimized RdCVFL (Nucleotides 23-655 of SEQ ID NO: 1 with an added 5' ATG codon) with the long form of native RdCVF SEQ ID NO: 3. Identities are 531/636 (83%). SEQ ID NO: 3 is the 636 nucleotide sequence of the native nucleic acid sequence encoding the long form of Homo sapiens nucleoredoxin-like 1 (NXNL1), including a start codon ATG at positions 1-3. Nucleotides 1-327 of SEQ ID NO: 3 are the short form of native RdCVF. The long form gene sequence is also reported at GenBank accession No. NM_138454.1.

FIG. 4 illustrates the alignment of the short form of optimized RdCVF (nucleotides 16-339 of SEQ ID NO: 2 with an added 5' ATG codon) with the short form of native RdCVF (nucleotides 1 to 327 of SEQ ID NO: 3). Identities are 271/327 (83%).

DETAILED DESCRIPTION

Figure 5:
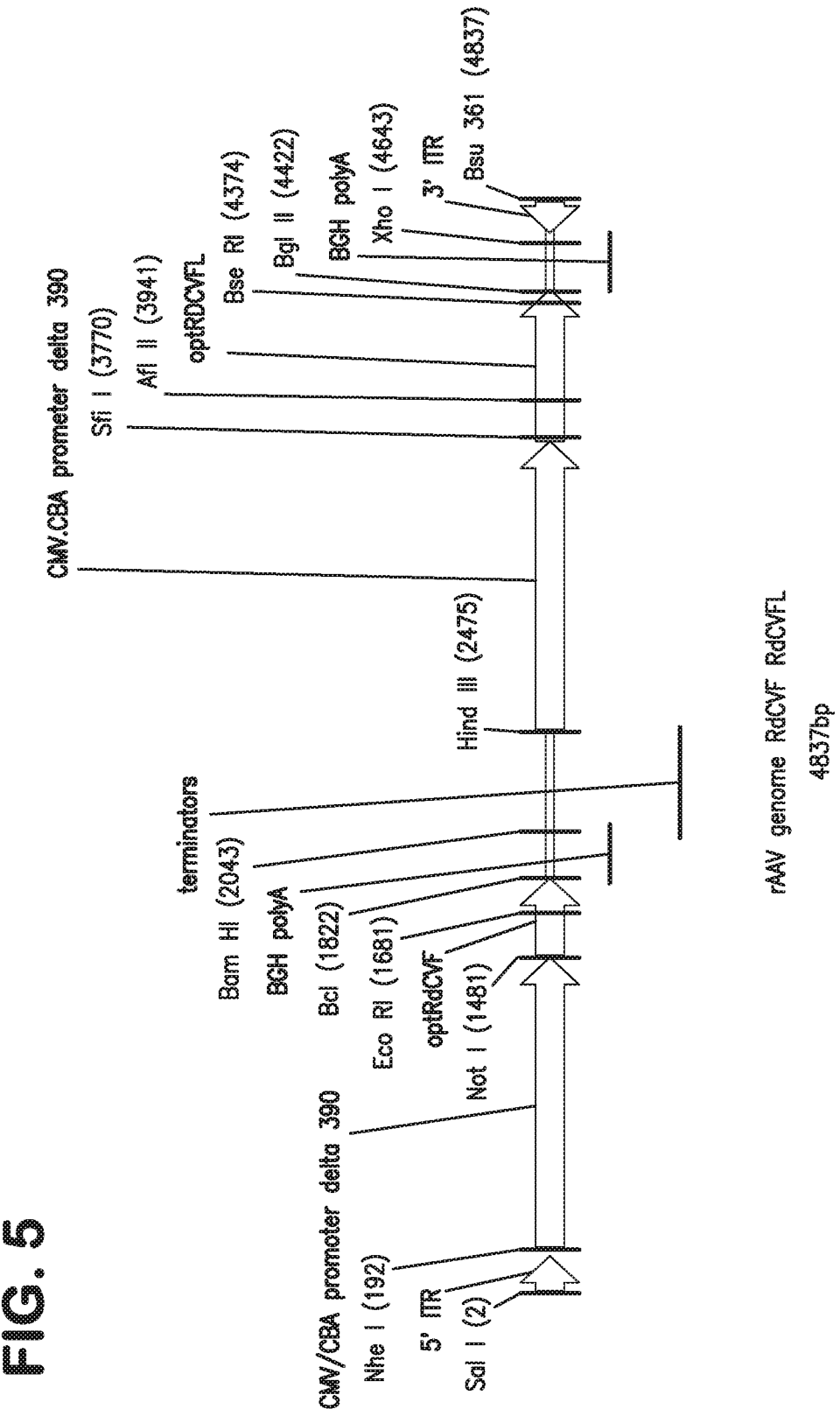
FIG. 5 is a schematic map of a single rAAV genome which contains between a 5' ITR and 3'ITR, an expression cassette containing tandem transgenes, i.e., the first transgene containing sequences (including a promoter and poly A sequence) necessary for expression of a codon optimized short form of RdCVF (optRdCVF) and the second transgene containing sequences (including a promoter and poly A sequence) necessary for expression of a codon optimized long form of RdCVFL (optRdCVFL).
Figure 6A:
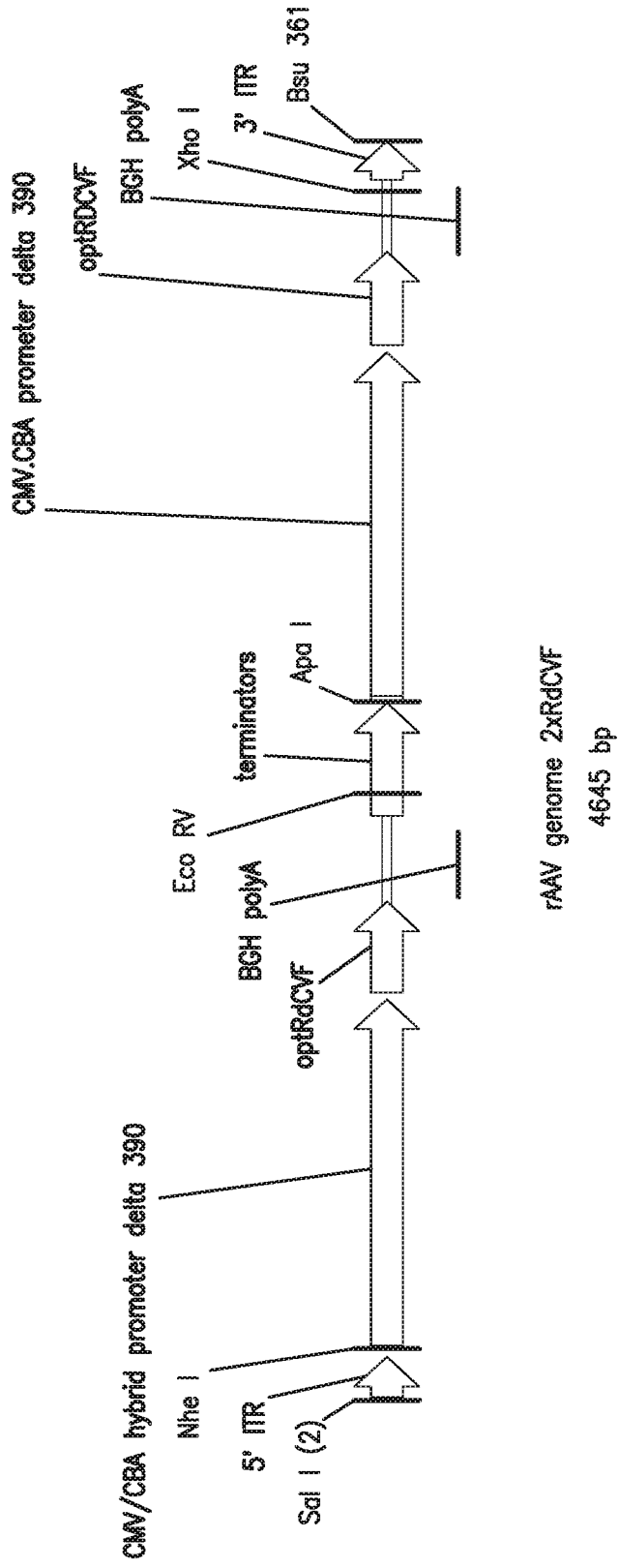
FIG. 6A is a schematic map of a single rAAV genome which contains between a 5' ITR and 3'ITR, an expression cassette containing tandem transgenes, i.e., the first transgene containing sequences (including a promoter and poly A sequence) necessary for expression of a codon optimized short form of RdCVF (optRdCVF) and the second transgene containing sequences (including a promoter and poly A sequence) necessary for expression of a second copy of the codon optimized short form of RdCVF (optRdCVF). This rAAV genome is referred to as 2xRdCVF.
Figure 6B:
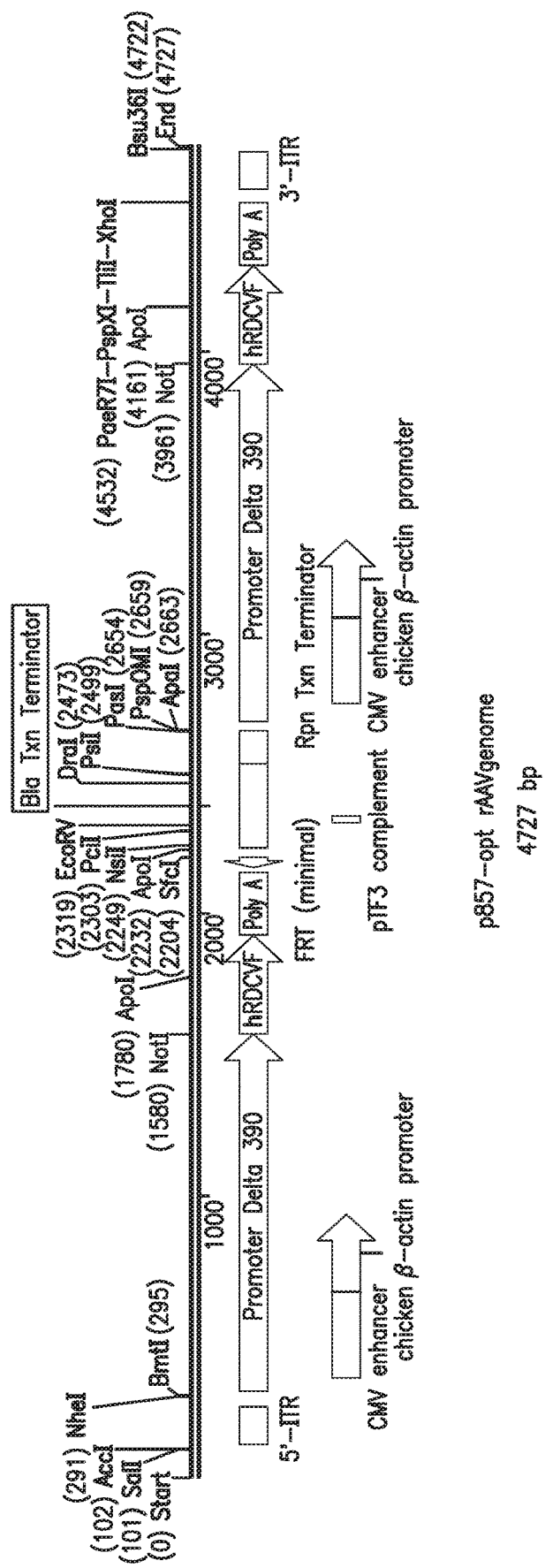
FIG. 6B is a more detailed map of the same rAAV genome of FIG. 6A.

The methods and compositions described herein involve compositions and methods for delivering optimized human rod-cone variability factors (hRdCVF) to mammalian subjects for the treatment of ocular disorders, primarily blinding diseases such as rod-cone dystrophies. The compositions and methods described herein involve expression cassettes, vectors, recombinant viruses and other compositions for delivery of multiple, different versions of the hRdCVF. Such compositions involve both codon optimization and the assembly of multiple, different versions of the hRdCVF, i.e., both the long and short forms or multiple copies of the same versions of RdCVF (multiple short or multiple long forms) in the same expression cassette, i.e., as tandem transgenes flanked by a single pair of ITR sequences within the same AAV genome, or vector or virus. These features not only increase the efficacy of the product but also, since a lower dose of reagent is used, increase safety. It is anticipated that this optimization of the transgene cassette could theoretically maximize the level of production of the experimental protein compared to levels that can be generated using the endogenous sequence.

The compositions and methods described herein, in one embodiment, are useful to prevent degeneration of cone photoreceptors in different genetic forms of retinal degeneration or in degenerative changes associated with other multi-systemic diseases (for example, diabetic retinopathy in diabetes).

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

NXNL1 is a member of the family rod-cone variability factor genes genes involved in a number of ocular diseases. This gene encodes for a long form, RdCVFL and a short form, RdCVF. The native nucleic acid sequence encoding human RdCVF, e.g., Homo sapiens nucleoredoxin-like 1 (NXNL1), is shown in SEQ ID NO: 3. See also GenBank accession No. NM_138454.1. See, also U.S. Pat. Nos. 7,795,387; 8,114,849, 8,394,756, as well as related patent disclosures, incorporated by reference for additional disclosure of this protein family. The short form of RdCVF is nucleotides 1-327 of SEQ ID NO: 3.

In certain embodiments of this invention, a subject has an "ocular disorder", for which the components, compositions and methods of this invention are designed to treat. As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, and others. As used herein, the term "subject" is used interchangeably with "patient".

As used herein "ocular disorder" includes, rod-cone dystrophies and retinal diseases including, without limitation, Stargardt disease (autosomal dominant or autosomal recessive), retinitis pigmentosa, age-related macular degeneration, rod-cone dystrophy, Leber's congenital amaurosis, Usher's syndrome, Bardet-Biedl Syndrome, Best disease, Bassen-Kornzweig syndrome, retinoschisis, untreated retinal detachment, pattern dystrophy, achromatopsia, choroideremia, ocular albinism, enhanced S cone syndrome, diabetic retinopathy, retinopathy of prematurity, sickle cell retinopathy, refsun syndrome, Congenital Stationary Night Blindness, glaucoma, gyrate atrophy or retinal vein occlusion. In another embodiment, the subject has, or is at risk of developing glaucoma, Leber's hereditary optic neuropathy, lysosomal storage disorder, or peroxisomal disorder. Clinical signs of such ocular diseases include, but are not limited to, decreased peripheral vision, decreased central (reading) vision, decreased night vision, loss of color perception, reduction in visual acuity, decreased photoreceptor function, pigmentary changes, and ultimately blindness.

As used herein, the term "treatment" or "treating" is defined encompassing administering to a subject one or more compounds or compositions described herein for the purposes of amelioration of one or more symptoms of an ocular disease. "Treatment" can thus include one or more of reducing onset or progression of an ocular disease, preventing disease, reducing the severity of the disease symptoms, or retarding their progression, including the progression of blindness, removing the disease symptoms, delaying onset of disease or monitoring progression of disease or efficacy of therapy in a given subject.

The term "exogenous" as used to describe a nucleic acid sequence or protein means that the nucleic acid or protein does not naturally occur in the position in which it exists in a chromosome, recombinant plasmid, vector or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

The terms "percent (%) identity", "sequence identity", "percent sequence identity", or "percent identical" in the context of nucleic acid sequences refers to the bases in the two sequences which are the same when aligned for correspondence. The percent identity is determined by comparing two sequences aligned under optimal conditions over the sequences to be compared. The length of sequence identity comparison may be over the full-length of the RdCVF and RdCVFL coding sequence, or a fragment of at least about 100 to 150 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Commonly available sequence analysis software, more specifically, BLAST or analysis tools provided by public databases may also be used.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

By "engineered" is meant that the nucleic acid sequences encoding the RdCVF (short form) and RdCVFL (long form) proteins described herein are assembled and placed into any suitable genetic element, e.g., naked DNA, phage, transposon, cosmid, episome, etc., which transfers the RdCVF sequences carried thereon to a host cell, e.g., for generating non-viral delivery systems (e.g., RNA-based systems, naked DNA, or the like) or for generating viral vectors in a packaging host cell and/or for delivery to a host cells in a subject. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012). The teachings of this specification coupled with known techniques permits one of skill in the art to reproduce the exemplified The term "transgene" as used herein means an exogenous or engineered protein-encoding nucleic acid sequence that is under the control of a promoter or expression control sequence in an expression cassette, rAAV genome, recombinant plasmid or proviral plasmid, vector, or host cell described in this specification. In certain embodiments, the transgene is a codon optimized RdCVFL encoding sequence SEQ ID NO: 1. In certain embodiments, the transgene is a codon optimized RdCVF (short form) encoding sequence SEQ ID NO:2. In other embodiments, both codon optimized and natural RdCVF and RdCVFL encoding sequences, in various combinations serve as the transgene.

A "vector" as used herein is a nucleic acid molecule into which an exogenous or heterologous or engineered nucleic acid transgene may be inserted which can then be introduced into an appropriate host cell. Vectors preferably have one or more origin of replication, and one or more site into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes." "Virus vectors" are defined as replication defective viruses containing the exogenous or heterologous RdCVF and RdCVFL nucleic acid transgene(s). In one embodiment a expression cassette as described herein may be engineered onto a plasmid which is used for drug delivery or for production of a viral vector. Suitable viral vectors are preferably replication defective and selected from amongst those which target ocular cells. Viral vectors may include any virus suitable for gene therapy may be used, including but not limited to adenovirus; herpes virus; lentivirus; retrovirus; parvovirus, etc. However, for ease of understanding, the adeno-associated virus is referenced herein as an exemplary virus vector.

A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In still another embodiment, the expression cassette, including any of those described herein is employed to generate a recombinant AAV genome.

As used herein, the term "host cell" may refer to the packaging cell line in which a recombinant AAV is produced from a proviral plasmid. In the alternative, the term "host cell" may refer to any target cell in which expression of the transgene is desired. Thus, a "host cell," refers to a prokaryotic or eukaryotic cell that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion.

In certain embodiments herein, the term "host cell" refers to cultures of ocular cells of various mammalian species for in vitro assessment of the compositions described herein. In other embodiments herein, the term "host cell" refers to the cells employed to generate and package the viral vector or recombinant virus. Still in other embodiments, the term "host cell" is intended to reference the ocular cells of the subject being treated in vivo for the ocular disease.

As used herein, the term "ocular cells" refers to any cell in, or associated with the function of, the eye. The term may refer to any one of photoreceptor cells, including rod, cone and photosensitive ganglion cells or retinal pigment epithelium (RPE) cells. In one embodiment, the ocular cells are the photoreceptor cells.

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As used herein, the term "transcriptional control sequence" or "expression control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "operably linked" or "operatively associated" refers to both expression control sequences that are contiguous with the nucleic acid sequence encoding the RdCVF and RdCVFL and/or expression control sequences that act in trans or at a distance to control the transcription and expression thereof.

The term "AAV" or "AAV serotype" as used herein refers to the more than 30 naturally occurring and available adeno-associated viruses, as well as artificial AAVs. Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, AAV1, AAV2, AAV3, AAV4, AAV5, AAV6, AAV6.2, AAV7, AAV8, AAV9, rh10, AAVrh64R1, AAVrh64R2, rh8, rh.10, variants of any of the known or mentioned AAVs or AAVs yet to be discovered or variants or mixtures thereof. See, e.g., WO 2005/033321. The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, Va.). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors.

"Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

By "administering" as used in the methods means delivering the composition to the target selected cell which is characterized by the ocular disease. In one embodiment, the method involves delivering the composition by subretinal injection to the photoreceptor cells or other ocular cells. In another embodiment, intravitreal injection to ocular cells is employed. In still another method, injection via the palpebral vein to ocular cells may be employed. Still other methods of administration may be selected by one of skill in the art given this disclosure. By "administering" or "route of administration" is delivery of composition described herein, with or without a pharmaceutical carrier or excipient, of the subject. Routes of administration may be combined, if desired. In some embodiments, the administration is repeated periodically. The pharmaceutical compositions described herein are designed for delivery to subjects in need thereof by any suitable route or a combination of different routes. Direct delivery to the eye (optionally via ocular delivery, intra-retinal injection, intravitreal, topical), or delivery via systemic routes, e.g., intraarterial, intraocular, intravenous, intramuscular, subcutaneous, intradermal, and other parental routes of administration. The nucleic acid molecules and/or vectors described herein may be delivered in a single composition or multiple compositions. Optionally, two or more different AAV may be delivered, or multiple viruses [see, e.g., WO20 2011/126808 and WO 2013/049493]. In another embodiment, multiple viruses may contain different replication-defective viruses (e.g., AAV and adenovirus), alone or in combination with proteins.

The terms "a" or "an" refers to one or more, for example, "an inhibitor" is understood to represent one or more such compounds, molecules, peptides or antibodies. As such, the terms "a" (or "an"), "one or more," and "at least one" are used interchangeably herein.

As used herein, the term "about" means a variability of plus or minus 10% from the reference given, unless otherwise specified.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

Certain compositions described herein are isolated, or synthetically or recombinantly engineered nucleic acid sequences that provide novel codon-optimized sequences encoding hRdCVFL (long form) and hRdCVF (short form). In one embodiment, an isolated or engineered codon optimized nucleic acid sequence encoding human RdCVFL long form is provided. This codon-optimized RdCVFL SEQ ID NO: 1 contains an N-terminal SfiI and Kozak and C-terminal BglII restrictions sites added for cloning. When aligned with the native nucleic acid sequence, the codon optimized RdCVFL may have a percent identity of at least 50%, or at least 60%, or at least 70%, or at least 80% or at least 90%, including any integer between any of those ranges. In one embodiment, the codon optimized RdCVFL has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%. In one embodiment, when aligned with the native nucleic acid sequence SEQ ID NO: 3, it is revealed that codon optimized RdCVFL SEQ ID NO: 1 has a percent sequence identity of only 83% (see FIG. 3).

In another embodiment, an isolated codon optimized nucleic acid sequence encoding human RdCVF short form is provided. When aligned with the native nucleic acid sequence, the codon optimized RdCVF may have a percent identity of at least 50%, or at least 60%, or at least 70%, or at least 80% or at least 90%, including any integer between any of those ranges. In one embodiment, the codon optimized RdCVF has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%. In one embodiment, the codon-optimized RdCVF SEQ ID NO: 2 contains N-terminal NotI and Kozak and C-terminal BclI restrictions sites added for cloning. When aligned with the native nucleic acid sequence (nucleotides 1-327 of SEQ ID NO: 3), it is revealed that the encoding sequence of SEQ ID NO: 2 has a percent sequence identity of only 83% with the short form of the native sequence (see FIG. 4).

In one embodiment, the optimized nucleic acid sequences encoding the hRdCVF long and/or short constructs described herein are engineered into any suitable genetic element, e.g., naked DNA, phage, transposon, cosmid, RNA molecule (e.g., mRNA), episome, etc., which transfers the RdCVF sequences carried thereon to a host cell, e.g., for generating nanoparticles carrying DNA or RNA, viral vectors in a packaging host cell and/or for delivery to a host cells in subject. In one embodiment, the genetic element is a plasmid.

The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

A variety of expression cassettes are provided which employ SEQ ID NOs. 1 and 2 for expression of multiple or different versions of the hRdCVF protein. As used herein, an "expression cassette" refers to a nucleic acid molecule which comprises coding sequences for the optimized RdCVFL and/or RdCVF (short) proteins, promoter, and may include other regulatory sequences therefor, which cassette may be engineered into a genetic element or plasmid, and/or packaged into the capsid of a viral vector (e.g., a viral particle). In one embodiment, an expression cassette comprises a codon optimized nucleic acid sequence, i.e., SEQ ID NO: 1, that encodes RdCVFL. In one embodiment, the cassette provides the codon optimized RdCVFL operatively associated with expression control sequences that direct expression of the codon optimized nucleic acid sequence that encodes RdCVFL in a host cell.

In another embodiment, an expression cassette comprises a codon optimized nucleic acid sequence, i.e., SEQ ID NO: 2, that encodes RdCVF. In one embodiment, the cassette provides the codon optimized RdCVF operatively associated with expression control sequences that direct expression of the codon optimized nucleic acid sequence that encodes RdCVF in a host cell.

In still another embodiment, an expression cassette comprises a codon optimized nucleic acid sequence that encodes RdCVFL and RdCVF. In one embodiment of such an expression cassette, the sequence encoding RdCVFL is operatively associated with the a first expression control sequence(s) that direct expression of the codon optimized nucleic acid sequence that encodes RdCVFL in a host cell (a first transgene) and the sequence encoding RdCVF is operatively associated with the a second expression control sequence(s) that direct expression of the codon optimized nucleic acid sequence that encodes RdCVF in a host cell (a second transgene). Transcription of each optimized sequence is controlled by an independent expression control sequence and the transgenes are in tandem orientation within a single rAAV genome or expression cassette In one embodiment, the second expression control sequence(s) are the copies of, but independent from, the first expression control sequence(s). In another embodiment, the second expression control sequence(s) are completely different and independent from, the first expression control sequence(s). In yet another embodiment, a single expression control sequence is operatively associated with both optimized sequences, so that both sequences are expressed at the same time under the same control sequences. In another embodiment, the two optimized sequences are expressed as a fusion sequence.

Further in one embodiment, the expression cassette comprises the hRdCVFL sequence under control of the first expression control sequence in position 5' to the hRdCVF sequence, which is under control of the second expression control sequence. In another embodiment, the expression cassette comprises the hRdCVF sequence under control of the second expression control sequence in position 5' to the hRdCVFL sequence, which is under control of the first expression control sequence. In yet another embodiment, where the expression cassette contains a single expression control sequence for control of transcription of both optimized sequences, the hRdCVF sequence is in position 5' to the hRdCVFL sequence or the hRdCVFL sequence is in position 5' to the hRdCVF sequence. In still other embodiments, the hRdCVF and hRdCVFL sequences may be in position to be expressed as a fusion protein.

In still another embodiment, an expression cassette comprises multiple copies of the RdCVF sequences, in which at one one copy is the codon optimized nucleic acid sequence, i.e., SEQ ID NO: 2, that encodes RdCVF. In one embodiment of such an expression cassette, the sequence encoding codon optimized RdCVF is operatively associated with the a first expression control sequence(s) that direct expression of the codon optimized nucleic acid sequence that encodes one copy of RdCVF in a host cell and the sequence encoding the second copy of codon-optimized RdCVF is operatively associated with a second expression control sequence(s) that direct expression of the codon optimized nucleic acid sequence that encodes the second copy of RdCVF in a host cell, i.e., transcription of each optimized sequence is controlled by an independent expression control sequence. In one embodiment, the second expression control sequence(s) are the copies of, but independent from, the first expression control sequence(s). In another embodiment, the second expression control sequence(s) are completely different and independent from, the first expression control sequence(s).

Similarly, in still another embodiment, an expression cassette comprises multiple copies of the RdCVFL sequences, in which at one one copy is the codon optimized nucleic acid sequence, i.e., SEQ ID NO: 1, that encodes RdCVFL. In one embodiment of such an expression cassette, the sequence encoding codon optimized RdCVFL is operatively associated with the a first expression control sequence(s) that direct expression of the codon optimized nucleic acid sequence that encodes one copy of RdCVFL in a host cell and the sequence encoding the second copy of codon-optimized RdCVFL is operatively associated with a second expression control sequence(s) that direct expression of the codon optimized nucleic acid sequence that encodes the second copy of RdCVFL in a host cell, i.e., transcription of each optimized sequence is controlled by an independent expression control sequence. In one embodiment, the second expression control sequence(s) are the copies of, but independent from, the first expression control sequence(s). In another embodiment, the second expression control sequence(s) are completely different and independent from, the first expression control sequence(s).

In yet another embodiment, a single expression control sequence is operatively associated with both optimized sequences, so that both sequences are expressed at the same time under the same control sequences. In another embodiment, the two optimized sequences are expressed as a fusion sequence. In still other embodiments, the optimized RdCVF is present in the expression cassette with a native version of the RdCVF sequence.

As described above for the expression cassettes containing both RdCVF and RdCVFL, in embodiments in which two different versions of RdCVF are employed, the codon optimized sequence may be positioned, 5' or 3' to another version of the short sequences. One of skill in the art may readily design constructs similar to those of the Examples below in view of the teachings of this specification.

As described herein, a "rAAV genome" is meant to describe an expression cassette or an expression cassette containing tandem transgenes, as described herein flanked on its 5' end by a 5'AAV inverted terminal repeat sequence (ITR) and on its 3' end by a 3' AAV ITR. Thus, this rAAV genome contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Each rAAV genome can be then introduced into a proviral plasmid following the teachings of WO2012/158757. The proviral plasmids are cultured in the host cells which express the AAV cap and/or rep proteins. In the host cells, each rAAV genome is rescued and packaged into the capsid protein or envelope protein to form an infectious viral particle.

In yet another embodiment, a vector comprising any of the expression cassettes described herein is provided. As described above, such vectors can be plasmids of variety of origins and are useful in certain embodiments for the generation of recombinant replication defective viruses as described further herein.

In one another embodiment, the vector is a proviral plasmid that comprises an AAV capsid and an recombinant AAV genome, wherein said rAAV genome comprises AAV inverted terminal repeat sequences and an expression cassette as described above comprising a codon optimized nucleic acid sequence that encodes RdCVFL, RdCVF, both RdCVFL and RdCVF or multiple (i.e., at least two) copies of RdCVF or two copies of RdCVFL, and expression control sequences that direct expression of the encoded protein in a host cell.

One type of proviral plasmid comprises a modular recombinant AAV genome that permits portions of the components of the rAAV genome to be removed and repeatedly replaced with other components without destroying the restriction sites in the plasmid. Such a proviral plasmid is one that contains a 5' AAV ITR sequence, the ITR flanked upstream by restriction site 1 and downstream by restriction site 2; a selected promoter flanked upstream by restriction site 2 and downstream by restriction site 3. Another component of the modular rAAV is a polylinker sequence comprising at least restriction site 3, restriction site 4 and restriction site 5, that contains a codon optimized nucleic acid sequence that encodes RdCVFL, a codon optimized nucleic acid sequence that encodes RdCVF, a codon optimized nucleic acid sequence that encodes RdCVFL and a codon optimized nucleic acid sequence that encodes RdCVF, or two or more copies of a sequence that encodes RdCVF, at least one such sequence being a codon optimized nucleic acid sequence encoding RdCVF. The RdCVF encoding sequences are located between any two of the restriction sites 3, 4 and 5, and are operatively linked to, and under the regulatory control of, the promoter. Alternatively, the second encoding sequence is inserted into the polylinker sequence along with the second expression control sequence of the expression cassette as described above.

Additional components of the modular rAAV include a polyadenylation sequence flanked upstream by restriction site 4 or 5 and downstream by restriction site 6; and a 3' AAV ITR sequence flanked upstream by restriction site 6 and downstream by restriction site 7. The proviral plasmid also contains elements necessary for replication in bacterial cells, and a resistance gene. Each of the above-noted restriction sites 1 through 7 occurs only once in the proviral plasmid and is cleaved by a different enzyme that cannot cleave another restriction site in the plasmid and thereby permit independent and repeated removal, replacement or substitution of the entire rAAV modular genome or only the elements flanked by those restriction sites from the plasmid. Such plasmids are described in detail in International Patent Application Publication No. WO2012/158757, incorporated by reference herein.

In still a further embodiment, a recombinant adeno-associated virus (AAV) vector is provided for delivery of the RdCVF constructs and optimized sequences described herein. An adeno-associated virus (AAV) viral vector is an AAV DNase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10). These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 vp3. In another embodiment, a self-complementary AAV is used.

For packaging an expression cassette or rAAV genome or proviral plasmid into virions, the ITRs are the only AAV components required in cis in the same construct as the transgene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or engineered obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

The rAAV vectors comprise an AAV capsid and an recombinant AAV genome, such as described above. In certain embodiments, the rAAV genome comprises AAV inverted terminal repeat sequences and an expression cassette comprising a codon optimized nucleic acid sequence that encodes RdCVFL, RdCVF, both RdCVFL and RdCVF or at least two copies of RdCVF, or two copies of RdCVFL, with at least one copy optimized or two copies optimized, and expression control sequences that direct expression of the encoded proteins in a host cell. The rAAV, in other embodiments, further comprises one or more of an intron, a Kozak sequence, a poly A, and post-transcriptional regulatory elements. Such rAAV vectors for use in pharmaceutical compositions for delivery to the eye, may employ a capsid from any of the many known AAVs identified above.

Other conventional components of the expression cassettes, rAAV genomes, and vectors include other components that can be optimized for a specific species using techniques known in the art including, e.g., codon optimization, as described herein. The components of the cassettes, vectors, plasmids and viruses or other compositions described herein include a promoter sequence as part of the expression control sequences. In one embodiment, a suitable promoter is a hybrid chicken (β-actin (CBA)promoter with cytomegalovirus (CMV) enhancer elements, such as the promoter used in the examples below and represented by the nucleic acid sequences of Tables 1 and 2A and 2B, i.e., nucleotides 307-1578 of SEQ ID NO: 5. Still other suitable promoters are the CB7 promoter, as well such as viral promoters, constitutive promoters, regulatable promoters [see, e.g., WO 2011/126808 and WO 2013/04943], or a promoter responsive to physiologic cues may be used may be utilized in the expression cassette, rAAV genomes, vectors, plasmids and viruses described herein.

In another embodiment, the promoter is cell-specific. The term "cell-specific" means that the particular promoter selected for the recombinant vector can direct expression of the optimized RdCVF transgene in a particular ocular cell type. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones.

Exemplary promoters may be the human G-protein-coupled receptor protein kinase 1 (GRK1) promoter (Genbank Accession number AY327580). In another embodiment, the promoter is a 292 nt fragment (positions 1793-2087) of the GRK1 promoter (See, Beltran et al, Gene Therapy 2010 17:1162-74, which is hereby incorporated by reference herein). In another preferred embodiment, the promoter is the human interphotoreceptor retinoid-binding protein proximal (IRBP) promoter. In one embodiment, the promoter is a 235 nt fragment of the hIRBP promoter. In one embodiment, the promoter is the RPGR proximal promoter (Shu et al, IOVS, May 2102, which is incorporated by reference herein). Other promoters useful in the invention include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12): 1015-23); the NXNL2/NXNL1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Each of these documents is incorporated by reference herein. In one embodiment, the promoter is of a small size, under 1000 bp, due to the size limitations of the AAV vector. In another embodiment, the promoter is under 400 bp. Other promoters may be selected by one of skill in the art.

In other embodiments, the cassette, vector, plasmid and virus constructs described herein contain other appropriate transcription initiation, termination, enhancer sequences, efficient RNA processing signals such as splicing and polyadenylation (poly A) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein. Examples of suitable poly A sequences include, e.g., SV40, bovine growth hormone (bGH), and TK poly A. Examples of suitable enhancers include, e.g., the CMV enhancer, the RSV enhancer, the alpha fetoprotein enhancer, the TTR minimal promoter/enhancer, LSP (TH-binding globulin promoter/alpha1-microglobulin/bikunin enhancer), amongst others.

In yet other aspects, these nucleic acid sequences, vectors, rAAV genomes and rAAV viral vectors are useful in a pharmaceutical composition, which also comprises a pharmaceutically acceptable carrier. Such pharmaceutical compositions are used to express the optimized RdCVFL or RdCVF, or multiple copies of RdCVF or both proteins in the ocular cells through delivery by such recombinantly engineered AAVs or artificial AAV's.

To prepare these pharmaceutical compositions containing the nucleic acid sequences, vectors, rAAV genomes and rAAV viral vectors, the sequences or vectors or viral vector is preferably assessed for contamination by conventional methods and then formulated into a pharmaceutical composition suitable for administration to the eye. Such formulation involves the use of a pharmaceutically and/or physiologically acceptable vehicle or carrier, particularly one suitable for administration to the eye, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In one exemplary specific embodiment, the composition of the carrier or excipient contains 180 mM NaCl, 10 mM NaPi, pH 7.3 with 0.0001%-0.01% Pluronic F68 (PF68). The exact composition of the saline component of the buffer ranges from 160 mM to 180 mM NaCl. Optional a different pH buffer (potentially HEPEs, sodium bicarbonate, TRIS) is used in place of the buffer specifically described. Still alternatively, a buffer containing 0.9% NaCl is useful.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The pharmaceutical compositions containing the replication-defective rAAV viruses can be formulated with a physiologically acceptable carrier for use in gene transfer and gene therapy applications. In the case of AAV viral vectors, quantification of the genome copies ("GC"), vector genomes, or virus particles may be used as the measure of the dose contained in the formulation or suspension. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal). In another method the effective dose of a recombinant adeno-associated virus carrying a nucleic acid sequence encoding the optimized RdCVF transgene under the desirably are measured as described in S. K. McLaughlin et al, 1988 J. Virol., 62:1963.

As used herein, the term "dosage" can refer to the total dosage delivered to the subject in the course of treatment, or the amount delivered in a single unit (or multiple unit or split dosage) administration. The pharmaceutical virus compositions can be formulated in dosage units to contain an amount of replication-defective virus carrying the codon optimized nucleic acid sequences encoding hRdCVF and/or hRdCVFL as described herein that is in the range of about $1.0 \times 10^9$ GC to about $1.0 \times 10^{15}$ GC including all integers or fractional amounts within the range. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

These above doses may be administered in a variety of volumes of carrier, excipient or buffer formulation, ranging from about 25 to about 1000 microliters, including all numbers within the range, depending on the size of the area to be treated, the viral titer used, the route of administration, and the desired effect of the method. In one embodiment, the volume of carrier, excipient or buffer is at least about 25 µl. In one embodiment, the volume is about 50 µl. In another embodiment, the volume is about 75 µl. In another embodiment, the volume is about 100 µl. In another embodiment, the volume is about 125 µl. In another embodiment, the volume is about 150 µl. In another embodiment, the volume is about 175 µl. In yet another embodiment, the volume is about 200 µL. In another embodiment, the volume is about 225 µl. In yet another embodiment, the volume is about 250 µl. In yet another embodiment, the volume is about 275 µl. In yet another embodiment, the volume is about 300 µL. In yet another embodiment, the volume is about 325 µL. In another embodiment, the volume is about 350 µl. In another embodiment, the volume is about 375 µl. In another embodiment, the volume is about 400 µl. In another embodiment, the volume is about 450 µl. In another embodiment, the volume is about 500 µl. In another embodiment, the volume is about 550 µl. In another embodiment, the volume is about 600 µl. In another embodiment, the volume is about 650 µl. In another embodiment, the volume is about 700 µl. In another embodiment, the volume is between about 700 and 1000 µl.

In one embodiment, the viral constructs may be delivered in concentrations of from at least least $1 \times 10^9$ to about least $1 \times 10^{11}$ GCs in volumes of about 1 µl to about 3 µl for small animal subjects, such as mice. For larger veterinary subjects having eyes about the same size as human eyes, the larger human dosages and volumes stated above are useful. See, e.g., Diehl et al, J. Applied Toxicology, 21:15-23 (2001) for a discussion of good practices for administration of substances to various veterinary animals. This document is incorporated herein by reference.

It is desirable that the lowest effective concentration of virus or other delivery vehicle be utilized in order to reduce the risk of undesirable effects, such as toxicity, retinal dysplasia and detachment. Still other dosages in these ranges may be selected by the attending physician, taking into account the physical state of the subject, preferably human, being treated, the age of the subject, the particular ocular disorder and the degree to which the disorder, if progressive, has developed.

Yet another aspect described herein is a method for treating, retarding or halting progression of blindness in a mammalian subject having one or more of the ocular diseases described above, such as rod-cone dystrophies or retinal degenerative disease. The rAAV, preferably suspended in a physiologically compatible carrier, diluent, excipient and/or adjuvant, may be administered to a desired subject including without limitation, a cat, dog, or other non-human mammalian subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of ocular diseases, and may also involve administration via the palpebral vein or other intravenous or conventional administration routes.

For use in these methods, the volume and viral titer of each dosage is determined individually, as further described herein, and may be the same or different from other treatments performed in the same, or contralateral, eye. In another embodiment, a single, larger volume treatment is made in order to treat the entire eye. The dosages, administrations and regimens may be determined by the attending physician given the teachings of this specification.

In one embodiment, the composition is administered in a single dosage selected from those above listed in a single affected eye. In another embodiment, the composition is administered as a single dosage selected from those above listed in a both affected eyes, either simultaneously or sequentially. Sequential administration may imply a time gap of administration from one eye to another from intervals of minutes, hours, days, weeks or months. In another embodiment, the method involves administering the compositions to an eye two or more dosages (e.g., split dosages).

In still other embodiments, the compositions described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

In certain embodiments of the invention it is desirable to perform non-invasive retinal imaging and functional studies to identify areas of the rod and cone photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc, depending upon the species of the subject being treated, their physical status and health and the dosage. In view of the imaging and functional studies, in some embodiments of the invention one or more injections are performed in the same eye in order to target different areas of the affected eye. The volume and viral titer of each injection is determined individually, as further described below, and may be the same or different from other injections performed in the same, or contralateral, eye. In another embodiment, a single, larger volume injection is made in order to treat the entire eye. In one embodiment, the volume and concentration of the rAAV composition is selected so that only the region of damaged rod and cone receptors is impacted. In another embodiment, the volume and/or concentration of the rAAV composition is a greater amount, in order reach larger portions of the eye, including non-damaged photoreceptors.

In one embodiment of the methods described herein, a one-time intra-ocular delivery of a composition such as those described herein, e.g., an AAV delivery of an optimized RdCVF or RdCVFL cassette, is useful in preventing vision loss and blindness in millions of individuals affected with such ocular disorders or multi-systemic diseases without regard to genotype or environmental exposure.

Thus, in one embodiment, the composition is administered before disease onset. In another embodiment, the composition is administered prior to the initiation of vision impairment or loss. In another embodiment, the composition is administered after initiation of vision impairment or loss. In yet another embodiment, the composition is administered when less than 90% of the rod and/or cones or photoreceptors are functioning or remaining, as compared to a non-diseased eye.

In another embodiment, the method includes performing additional studies, e.g., functional and imaging studies to determine the efficacy of the treatment. For examination in animals, such tests include retinal and visual function assessment via electroretinograms (ERGs) looking at rod and cone photoreceptor function, optokinetic nystagmus, pupillometry, water maze testing, light-dark preference histology (retinal thickness, rows of nuclei in the outer nuclear layer, immunofluorescence to document transgene expression, cone photoreceptor counting, staining of retinal sections with peanut agglutinin—which identifies cone photoreceptor sheaths). Other suitable tests of efficacy are sampling of anterior chamber fluid to document presence of the RdCVF and RdCVFL transgenic proteins.

Specifically for human subjects, following administration of a dosage of a compositions described in this specification, the subject is tested for efficacy of treatment using electroretinograms (ERGs) to examine rod and cone photoreceptor function, pupillometry visual acuity, contrast sensitivity color vision testing, visual field testing (Humphrey visual fields/Goldmann visual fields), perimetry mobility test (obstacle course), and reading speed test. Other useful post-treatment efficacy test to which the subject is exposed following treatment with a pharmaceutical composition described herein are functional magnetic resonance imaging (fMRI), full-field light sensitivity testing, retinal structure studies including optical coherence tomography, fundus photography, fundus autofluorescence, adaptive optics scanning, and/or laser ophthalmoscopy. These and other efficacy tests are described in U.S. Pat. No. 8,147,823; in co-pending International patent application publication WO 2014/011210 or WO 2014/124282, incorporated by reference.

In yet another embodiment, any of the above described methods is performed in combination with another, or secondary, therapy. In still other embodiments, the methods of treatment of these ocular diseases involve treating the subject with the composition described in detail herein in combination with another therapy, such as antibiotic treatment, palliative treatment for pain, and the like. The additional therapy may be any now known, or as yet unknown, therapy which helps prevent, arrest or ameliorate these mutations or defects or any of the effects associated therewith. The secondary therapy can be administered before, concurrent with, or after administration of the compositions described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In one embodiment, a method of generating a recombinant rAAV comprises obtaining a plasmid containing a rAAV genome as described above and culturing a packaging cell carrying the plasmid in the presence of sufficient viral sequences to permit packaging of the AAV viral genome into an infectious AAV envelope or capsid. Specific methods of rAAV vector generation are described above and may be employed in generating a rAAV vector that can deliver one or more of the codon optimized RdCVFL or RdCVF in the expression cassettes and genomes described above and in the examples below.

The following examples disclose specific embodiments of the nucleic acid sequences, expression cassettes, rAAV genome and viral vectors for use in treating the ocular diseases specified herein. These specific embodiments illustrate various aspects of the invention. These examples should be construed to encompass any and all variations that become evident as a result of the teaching provided herein.

Example 1

Codon Optimized Sequences

The nucleic acid sequence SEQ ID NO: 1 (FIG. 1) encoding codon optimized human RdCVFL was generated to add N-terminal restriction site SfiI and C terminal restriction site BglII, as well as Kozak sequences. The open reading frame (ORF) of codon optimized SEQ ID NO:1 differs from the native sequence by 17%, i.e., it shares only 83% identity with native hRdCVF, as shown in FIG. 3.

The nucleic acid sequence SEQ ID NO: 2 (FIG. 1) encoding codon optimized human RdCVF was generated to add N-terminal restriction site NotI and C terminal restriction site BclII, as well as Kozak sequences. The ORF of codon optimized SEQ ID NO:2 differs from the native sequence by 17%, sharing only 83% identity with native hRdCVF, as shown in FIG. 4.

Example 2

Construction of P853

SEQ ID NO: 2 was cloned into an expression vector under the control of a chicken-beta actin promoter with CMV enhancer, the promoter truncated by 390 nucleotides. SEQ ID NO: 1 was cloned into the same cassette under the control of a second copy of the same promoter. The expression construct was flanked by AAV2 ITRs thus forming the p853 rAAV genome p853 (See FIG. 5). This rAAV genome was then inserted into a proviral plasmid, p618 containing a lambda stuffer sequence (see International Patent Application Publication No. WO2012/158757A1), thereby generating the proviral plasmid p853 which permits expression of both the long and short RdCVF proteins in a single vector.

The features of the rAAV genome of FIG. 5 SEQ ID NO: 4 and the p853 plasmid pAAV.CMV.CBA.hRdCVF.CMV.CBA.hRDCVFL.SYNITR.Long SEQ ID NO: 7 containing the rAAV genome of FIG. 5 and other plasmid sequences are described below in Table 1, with reference to the nucleotide positions (Nts) in each sequence.

TABLE 1

SEQUENCES

| Sequence Feature | rAAV Genome Cassette Nts of SEQ ID NO: 4 | pAAV.CMV.CBA.hRdCVF.CMV.CBA.hRdCVFL.SYNITR.long Nts of SEQ ID NO: 7 |
| --- | --- | --- |
| Kan$^R$ Complement | — | 9-803 |
| B1 B2 T1 Txn Terminator Complement | — | 988-1162 |
| pTR | — | 1063-1079 |
| 5' ITR (D Segment) | 17-146 (129-146) | 1253-1382 (1365-1382) |
| Promoter Delta 390 | 207-1478 | 1443-2714 |
| hRdCVF | 1479-1826 | 2715-3062 |
| Poly A | 1821-2047 | 3057-3283 |
| Terminator (Promoter) With Flanking Restriction Sites | 2042-2479 (2490-3761) 2474-3774 | 3278-3715 (3726-4997) 3710-5010 |
| hRDCVFL | 3762-4426 (BgI) | 4998-5662 |
| Poly A | 4427-4643 | 5663-5879 |
| 3' ITR (D Segment) | 4691-4820 (4691-4708) | 5927-6056 (5927-5944) |
| pTF3 Complement | — | 6241-6266 |
| BLA Txn Terminator | — | 6150-6450 |
| RPN Txn Terminator | — | 6457-6570 |
| Lambda Stuffer | — | 6586-11652 |
| pUC Ori Complement | — | 11813-12616 |

Example 3

Construction of rAAV Co-Expressing hRdCVF and hRdCVFL

The rAAV genome from this p853 proviral plasmid SEQ ID NO: 7 is packaged in a selected AAV capsid by culturing a packaging cell carrying the plasmid in the presence of sufficient viral sequences to permit packaging of the AAV genome into an infectious AAV envelope or capsid. In one embodiment, a method for producing the rAAV involves packaging in a stable rep and cap expressing mammalian host packaging cell line (such as B-50 as described in International Patent Application Publication No. WO 99/15685) with the adenovirus E1, E2a, and E4ORF6 DNA. Iodixanol gradient purification is followed by herparinsepharose agarose column chromatography. Vector titers are determined using an infectious center assay.

Recombinant AAV.CMV.CBA.hRdCVF.CMV.CBA.hRd-CVFL. SYNITR.Long virus preparations are prepared in and combined to a desired total volume.

Still other methods of producing such rAAV particles involve use of an insect cell packaging cell line, such as described in Smith et al, ref 11, cited below.

The AAV.CMV.CBA.hRdCVF.CMV.CBA.hRdCVFL-.SYNITR.Long viral particles are suspended in a suitable excipient, such as 180 mM NaCl, 10 mM NaPi, pH7.3, containing 0.0001%-0.01% Pluronic F68 (PF68). The composition of the saline component ranges from 160 mM to 180 mM NaCl. Other buffers are useful in such compositions, including HEPEs, sodium bicarbonate, TRIS, or 0.9% NaCl solution.

Several preparations of the rAAV are combined to a desired total volume. In one embodiment, a total volume is a dosage of $1 \times 10^{11}$ GC in a volume of 300 microliters of buffer. Contaminating helper adenovirus and native AAV, assayed by serial dilution cytopathic effect or infectious center assay, respectively are anticipated to be less than one or multiples orders of magnitude lower than vector AAV.

Example 4

Construction of rAAV Expressing 2XRdCVF

A native short form of RdCVF (or the codon optimized SEQ ID NO: 2) was cloned into an expression vector under the control of a chicken-beta actin promoter with CMV enhancer, the promoter truncated by 390 nucleotides. A second copy of the native sequence of RdCVF (or the codon optimized SEQ ID NO: 2) was cloned into the same cassette under the control of a second copy of the same promoter. The expression construct was flanked by AAV2 ITRs thus forming the rAAV genome 2xRdCVF. The rAAV genome with native RdCVF sequences is reported in SEQ ID NO: 5. The rAAV genome with codon optimized sequences is reported as SEQ ID NO: 8. Either of these rAAV genomes was then inserted into a proviral plasmid, p617 (see International Patent Application Publication No. WO2012/158757A1), thereby generating the proviral plasmid SEQ ID NO: 6 (with native RdCVF) or the proviral plasmid p857 of SEQ ID NO: 9 (codon optimized RdCVF) which permits expression of two copies of the short RdCVF protein in a single vector.

The features of the rAAV genome 2xRdCVF containing the native sequences SEQ ID NO: 5) and the plasmid called pAAV.CMV.CBA.delta390.hRdCVFL.2x.synITR.long—native RdCVF (SEQ ID NO: 6) are described below in Table 2A, with reference to the nucleotide positions (Nts) in each sequence.

TABLE 2A

| SEQUENCES | | |
|---|---|---|
| Sequence Feature | rAAV genome 2xRdCVF - native sequence Nts Of SEQ ID NO: 5 | pAAV.CMV.CBA.delta-390.hRdCVF1.2x.-synITR.long - native sequences Nts Of SEQ ID NO: 6 |
| Kan$^R$ complement | 9-100 | 9-803 |
| B1 B2 T1 Txn Terminator Complement | — | 988-1162 |
| pTR | — | 1063-1079 |
| 5 ITR (D segment) | 117-246 (229-246) | 1253-1382 (1365-1382) |
| Promoter Delta 390 | 307-1578 | 1443-2714 |
| hRdCVF | 1591-1935 | 2727-3071 |
| Poly A | 1940-2161 | 3076-3297 |
| pTF3 complement | 2337-2362 | 3473-3498 |
| Bla Txn Terminator | 2246-2546 | 3382-3682 |
| Rpn Txn Terminator | 2553-2666 | 3689-3802 |
| Promoter | 2697-3968 | 3833-5104 |
| hRDCVF | 3981-4325 | 5117-5461 |
| Poly A | 4330-4551 | 5466-5687 |
| 3' ITR | 4599-4728 | 5735-5864 |
| BLA Txn Terminator | — | 5958-6258 |
| pTF3 Complement | — | 6049-6074 |
| Rpn Txn Terminator | — | 6265-6378 |
| Lambda Stuffer | — | 6394-11460 |
| pUC Ori Complement | — | 11621-12424 |

The features of the rAAV genome 2xRdCVF containing the codon optimized sequences of RdCVF (SEQ ID NO: 8) and p857opt plasmid called pAAV.CMV.CBA.delta390.hRdCVFL.2x.synITR.long (SEQ ID NO: 9) are described below in Table 2B, with reference to the nucleotide positions (Nts) in each sequence.

TABLE 2B

| p857opt SEQUENCES | | |
|---|---|---|
| Sequence Feature | rAAV genome cassette Nts Of SEQ ID NO: 8 | pAAV.CMV.CBA.delta-390.hRdCVF1.2x.-synITR.long Nts Of SEQ ID NO: 9 |
| Kan$^R$ complement | 9-100 | 9-803 |
| B1 B2 T1 Txn Terminator Complement | — | 988-1162 |
| pTR | — | 1063-1079 |
| 5' ITR (D segment) | 117-246 (229-246) | 1253-1382 (1365-1382) |
| Promoter Delta 390 | 307-1578 | 1443-2714 |
| hoptRdCVF | 1579-1926 | 2715-3062 |
| Poly A | 1931-2152 | 3067-3288 |
| pTF3 complement | 2328-2353 | 3464-3489 |
| Bla Txn Terminator | 2237-2537 | 3373-3673 |
| Rpn Txn Terminator | 2544-2657 | 3680-3793 |
| Promoter | 2688-3959 | 3824-5095 |
| hoptRDCVF | 3960-4307 | 5096-5443 |
| Poly A | 4312-4533 | 5448-5669 |
| 3' ITR | 4581-4710 | 5717-5846 |
| BLA Txn Terminator | — | 5940-6240 |
| pTF3 Complement | — | 6031-6056 |
| Rpn Txn Terminator | — | 6247-6360 |
| Lambda Stuffer | — | 6376-11442 |
| pUC Ori Complement | — | 11603-12406 |

Example 5

Construction of rAAV Co-Expressing Two Copies of hRDCVF

The rAAV genome from the proviral plasmids of SEQ ID NO: 8 or SEQ ID NO: 9 is packaged in a selected AAV capsid by culturing a packaging cell carrying the plasmid in the presence of sufficient viral sequences to permit packaging of the AAV genome into an infectious AAV envelope or capsid. In one embodiment, a method for producing the rAAV involves packaging in a stable rep and cap expressing mammalian host packaging cell line (such as B-50 as described in International Patent Application Publication No. WO 99/15685) with the adenovirus E1, E2a, and E4ORF6 DNA. Iodixanol gradient purification is followed by heparin-sepharose agarose column chromatography. Vector titers are determined using an infectious center assay.

AAV.CMV.CBA.delta390.hRdCVF1.2x.synITR.long virus (native or codon optimized) preparations are prepared and suspended in a suitable excipient, such as 180 mM NaCl, 10 mM NaPi, pH7.3, containing 0.0001%-0.01% Pluronic F68 (PF68). The composition of the saline component ranges from 160 mM to 180 mM NaCl. Other buffers are useful in such compositions, including HEPEs, sodium bicarbonate, TRIS, or 0.9% NaCl solution.

Several preparations of the rAAV are combined to a desired total volume. In one embodiment, a total volume is 1.0 to $10^5$ ml containing either a dose of $2.3 \times 10^{11}$ infectious particles or viral genomes or a concentration of $2.3 \times 10^{11}$ infectious particles or viral genomes/ml. Contaminating helper adenovirus and native AAV, assayed by serial dilution cytopathic effect or infectious center assay, respectively are anticipated to be orders of magnitude lower than vector AAV.

In a similar manner an rAAV containing tandem expression of two copies of the long form of RdCVF (2xRdCVFL) and corresponding plasmid are generated.

Still other methods of producing such rAAV particles involve use of an insect cell packaging cell line, such as described in Smith et al, ref 11, cited below.

Example 6

In Vitro And In Vivo Tests

The suspension of rAAV particles described in Examples 1 through 5 are employed to transduce target cell cultures in vitro, such as in mice or chicken retinal cell cultures, at multiplicities of infection (MOI) ranging from $10^3$ to $10^6$ rAAV viral particles per cell. Survival counts of cone photoreceptors from such species are counted to demonstrate the efficacy of gene transfer. Other suitable techniques for determining efficacy in such in vitro models are RT-PCR, immunocytochemistry, immunohisto-chemistry, and Western blot analysis.

The rAAV particles are also employed to transduce cells of the murine or other mammalian (e.g., canine or feline) retina after administration by subretinal injection of $10^{11}$-$10^{13}$ viral particles or $10^{11}$-$10^{13}$ viral particles/ml buffer. Expression of both hRdCVFL and hRdCVF together in transduced cells or retinas or expression of two copies of hRdCVF is assessed by retinal and visual function. These functions may be examined in animals using one or more of the techniques: electroretinograms (ERGs) looking at rod and (especially) cone photoreceptor function, optokinetic nystagmus, pupillometry, water maze testing, light-dark preference histology (retinal thickness, rows of nuclei in the outer nuclear layer, immunofluorescence to document transgene expression, cone photoreceptor counting, staining of retinal sections with peanut agglutinin—which identifies cone photoreceptor sheaths). Additionally, sampling of anterior chamber fluid is used to document the presence of the RdCVF transgenic protein.

Example 7

Efficacy In Human Subjects

The rAAV particles are also employed to transduce cells of human subject's retina after administration by subretinal injection of $10^{10}$-$10^{12}$ GC or viral particles in a suspension in a suitable buffered carrier. Expression of both hRdCVFL and hRdCVF together in transduced cells or retinas or expression of two copies of hRdCVF is assessed by retinal and visual function.

These functions may be examined in humans using one or more of the techniques: electroretinograms (ERGs) looking at rod and cone photoreceptor function pupillometry visual acuity contrast sensitivity color vision testing visual field testing (Humphrey visual fields/Goldmann visual fields) perimetry mobility test (obstacle course) reading speed test. Other useful tests include functional magnetic resonance imaging (fMRI) full-field light sensitivity testing, retinal structure studies including optical coherence tomography, fundus photography, fundus autofluorescence, adaptive optics and scanning laser ophthalmoscopy.

Methods of use of these recombinant viruses are introduced into human subjects and evaluated by techniques, such as described in the examples described in published international applications WO2016/185037 and WO2016/185242, incorporated by reference herein.

Each and every patent, patent application, and publication, including websites cited throughout specification, as well as U.S. provisional patent application No. 62/275,006, are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

TABLE 3

(Sequence Listing Free Text)
The following information is provided for sequences containing free text under numeric identifier <223>.

| SEQ ID NO: (containing free text) | Free text under <223> |
|---|---|
| 4 | rAAV genome with ITRs flanking an expression cassette containing RdCVF sequences and promoters |
| 4 | AAV 5' ITR |
| 4 | hRdCVF short form codon optimized |
| 4 | hRdCVFL long form codon optimized |
| 4 | AAV 3' ITR |
| 5 | p857 rAAV genome with two copies of RdCVF and promoters |
| 5 | KanR complement |
| 5 | AAV 5' ITR |
| 5 | human RdCVF native short form |
| 5 | pTF3 complement |
| 5 | human RdCVF native short form second copy |

TABLE 3-continued (Sequence Listing Free Text)
The following information is provided for sequences containing free text under numeric identifier <223>.

| SEQ ID NO: (containing free text) | Free text under <223> |
|---|---|
| 5 | AAV 3' ITR |
| 6 | Plasmid containing the p857 rAAV genome containing native 2xRdCVF |
| 6 | KanR complement |
| 6 | pTR |
| 6 | AAV 5 ITR |
| 6 | B1 B2 T1 Txn Terminator Complement |
| 6 | hRdCVF (native short form) |
| 6 | pTF3 complement |
| 6 | hRdCVF native short form second copy |
| 6 | AAV 3' ITR |
| 6 | pTF3 Complement |
| 6 | Lambda Stuffer |
| 6 | pUC Ori Complement |
| 7 | Plasmid containing the rAAV genome of p853 |
| 7 | KanR complement |
| 7 | B1 B2 T1 Txn Terminator Complement |
| 7 | pTR |
| 7 | AAV 5' ITR |
| 7 | human hRdCVF short form optimized sequence |
| 7 | hRDCVFL optimized sequence long form |
| 7 | AAV 3' ITR |
| 7 | pTF3 Complement |
| 7 | Lambda Stuffer |
| 7 | pUC Ori Complement |
| 8 | rAAV genome expressing two copies of human RdCVF codon optimized short form sequences |
| 8 | KanR complement |
| 8 | AAV 5' ITR |
| 8 | human optimized RdCVF short form |
| 8 | pTF3 complement |
| 8 | human optimized RdCVF short form second copy |
| 8 | AAV 3' ITR |
| 9 | plasmid expressing rAAV genome with two copies of optimized human RdCVF short form |
| 9 | KanR complement |
| 9 | pTF3 complement |
| 9 | B1 B2 T1 Txn Terminator Complement |
| 9 | pTR |
| 9 | 5' AAV ITR |
| 9 | human optimized RdCVF short form |
| 9 | human optimized RdCVF short form second copy |
| 9 | AAV 3' ITR |
| 9 | pTF3 Complement |
| 9 | Lambda Stuffer |
| 9 | pUC Ori Complement |

REFERENCES

1. U.S. Pat. No. 7,795,387
2. U.S. Pat. No. 8,114,849
3. U.S. Pat. No. 8,394,756
4. U.S. Pat. No. 8,518,695
5. U.S. Pat. No. 8,957,043
6. US Patent Appin Publication No. 2009062188A1
7. Natalia Caporale et al, July 2011, LiGluR Restores Visual Responses in Rodent Models of Inherited Blindness, *Mol. Therapy*, 19(7):1212-1219
8. Kotin, R M, April 2011 Large-scale recombinant adeno-associated virus production., *Hu. Mol. Genet*, 20(1): R1-R6
9. Byrne et al, January 2015, "Viral-mediated RdCVF and RdCVFL expression protects cone and rod photoreceptors in retinal degeneration", *J. Clin. Invest.*, 125(1):105-116
10. Maguire, A M et al., October 2009 Age-dependent effects of RPE65 gene therapy for Leber's congenital amaurosis: a phase 1 dose-escalation trial. *Lancet*, DOI:10.1016/S0140-6736(09)61836-5
11. Smith, R H et al, June 2009 A Simplified Baculovirus-AAV Expression Vector System Coupled With One-step Affinity Purification Yields High-titer rAAV Stocks From Insect Cells, *Mol. Ther.*, 17(11): 1889-1896
12. Bennicelli J et al, March 2008 Reversal of Blindness in Animal Models of Leber Congenital Amaurosis Using Optimized AAV2-mediated Gene Transfer, *Mol. Ther.*, 16(3):458-465
13. International Patent Application Publication No. WO2013/063383
14. International Patent Application Publication No. WO2016/185037
15. International Patent Application Publication No. WO2016/185242

The invention claimed is:

1. An expression cassette comprising one or more of:
    (a) the nucleic acid sequence set forth in SEQ ID NO: 1,
    (b) the nucleic acid sequence set forth in SEQ ID NO: 2,
    (c) the nucleic acid sequence set forth in SEQ ID NO: 1 and the nucleic acid sequence set forth in SEQ ID NO: 2; and
    (d) two copies of the nucleic acid sequence set forth in SEQ ID NO: 2,
    wherein the nucleic acid sequence set forth in SEQ ID NO: 1 encodes RdCVFL and the nucleic acid sequence set forth in SEQ ID NO: 2 encodes RdCVF.

2. The expression cassette according to claim 1, wherein each nucleic acid sequence is operatively associated with an expression control sequence that directs expression in a host cell.

3. A recombinant AAV (rAAV) vector, wherein said rAAV vector comprises AAV inverted terminal repeat sequences flanking the expression cassette of claim 1.

4. A vector or plasmid comprising the expression cassette of claim 1.

5. An rAAV vector comprising AAV inverted terminal repeat sequences and an expression cassette comprising at least one of the nucleic acid sequences set forth in SEQ ID NO: 1 or SEQ ID NO: 2 and expression control sequences that direct expression of said nucleic acid sequences in a host cell.

6. The rAAV vector of claim 5, comprising a 5' AAV ITR sequence, a first CMV/CBA promoter, a first nucleic acid sequence set forth in SEQ ID NO: 1 or 2, a first polyadenylation sequence, transcriptional terminator sequences a second CMV/CBA promoter, a second nucleic acid sequence set forth in SEQ ID NO: 1 or 2, a second polyadenylation sequence and a 3' AAV ITR sequence.

7. An isolated host cell comprising the expression cassette of claim 1.

8. A composition comprising an engineered nucleic acid molecule for use in the treatment of an ocular disease comprising:
    (a) the nucleic acid sequence set forth in SEQ ID NO: 1,
    (b) the nucleic acid sequence set forth in SEQ ID NO: 2,
    (c) the nucleic acid sequence set forth in SEQ ID NO: 1 and the nucleic acid sequence set forth in SEQ ID NO: 2; or
    (d) two copies of the nucleic acid sequence set forth in SEQ ID NO: 1 or SEQ ID NO: 2,
    wherein each nucleic acid sequence is under the control of expression control sequences which direct expression of the encoded RdCVFL or RdCVF in ocular cells; and a carrier suitable for delivery to the eye of a subject.

9. A composition comprising a pharmaceutically acceptable carrier suitable for delivery to the eye and the rAAV vector of claim 5.

* * * * *

SEQUENCE LISTING

```
<160> NUMBER OF SEQ ID NOS: 9

<210> SEQ ID NO 1
<211> LENGTH: 665
<212> TYPE: DNA
<213> ORGANISM: Homo sapiens
<220> FEATURE:
<221> NAME/KEY: exon
<222> LOCATION: (23)..(655)

<400> SEQUENCE: 1
ggccatacag gccgccacca tg gcc tca ctg ttc tcc ggg cgc atc ctc atc      52
                         Ala Ser Leu Phe Ser Gly Arg Ile Leu Ile
                          1               5                  10 cga aac aac agc gat cag gac gaa ttg gac acc gag gct gaa gtc tcc     100
Arg Asn Asn Ser Asp Gln Asp Glu Leu Asp Thr Glu Ala Glu Val Ser
             15                  20                  25
```

```
cgc cgg ctg gaa aac agg ctc gtg ctc ctg ttc ttc ggt gcc gga gcg      148
Arg Arg Leu Glu Asn Arg Leu Val Leu Leu Phe Phe Gly Ala Gly Ala
            30                  35                  40 tgc ccg cag tgc caa gcc ttc gtc cca att ctt aag gac ttc ttt gtg      196
Cys Pro Gln Cys Gln Ala Phe Val Pro Ile Leu Lys Asp Phe Phe Val
        45                  50                  55 cgc ctc act gat gag ttt tac gtg ctc cgg gca gcg cag ctg gcc ttg      244
Arg Leu Thr Asp Glu Phe Tyr Val Leu Arg Ala Ala Gln Leu Ala Leu
    60                  65                  70 gtg tat gtg tcg caa gat tcc act gag gaa caa cag gac ctg ttc ctg      292
Val Tyr Val Ser Gln Asp Ser Thr Glu Glu Gln Gln Asp Leu Phe Leu
75                  80                  85                  90 aaa gac atg cct aag aag tgg ctt ttc ctg ccc ttc gag gac gac ctg      340
Lys Asp Met Pro Lys Lys Trp Leu Phe Leu Pro Phe Glu Asp Asp Leu
                95                  100                 105 aga agg gac ctg gga cgc cag ttc agc gtg gaa cgg ctg ccg gcc gtc      388
Arg Arg Asp Leu Gly Arg Gln Phe Ser Val Glu Arg Leu Pro Ala Val
            110                 115                 120 gtg gtg ctg aag ccc gac ggg gac gtg ctt acc cgg gat ggc gct gac      436
Val Val Leu Lys Pro Asp Gly Asp Val Leu Thr Arg Asp Gly Ala Asp
        125                 130                 135 gaa atc cag agg ctg ggc acc gcc tgt ttc gca aat tgg cag gag gcc      484
Glu Ile Gln Arg Leu Gly Thr Ala Cys Phe Ala Asn Trp Gln Glu Ala
    140                 145                 150 gcc gaa gtg ctc gac cgg aac ttc cag ctg ccc gag gat ctg gag gac      532
Ala Glu Val Leu Asp Arg Asn Phe Gln Leu Pro Glu Asp Leu Glu Asp
155                 160                 165                 170 cag gaa cct cgg tcc ctg acc gag tgc ctc aga cgc cac aag tac cgc      580
Gln Glu Pro Arg Ser Leu Thr Glu Cys Leu Arg Arg His Lys Tyr Arg
                175                 180                 185 gtg gaa aag gcc gcg aga gga gga cgg gac ccg ggt ggc ggg gga ggc      628
Val Glu Lys Ala Ala Arg Gly Gly Arg Asp Pro Gly Gly Gly Gly Gly
            190                 195                 200 gaa gag ggc gga gcc ggt ggc ctg ttc tgatagatct                       665
Glu Glu Gly Gly Ala Gly Gly Leu Phe
        205                 210

<210> SEQ ID NO 2
<211> LENGTH: 348
<212> TYPE: DNA
<213> ORGANISM: Homo sapiens

<400> SEQUENCE: 2
gcggccgcca ccatggccag cctcttctcc ggacgcatcc tgattcgcaa caattccgac     60
caagacgaac tggataccga ggccgaagtc tcgcggagat tggagaacag gcttgtgctg    120
ctgttctttg gcgcgggagc gtgtcctcag tgccaggctt tcgtgccaat cctgaaggat    180
ttcttcgtgc ggctgactga cgaattctac gtcctccggg ccgcccagct ggcactggtg    240
tacgtgtccc aagactcaac cgaggaacag caggatctgt tcctcaagga catgcccaaa    300
aagtggctgt tcctgccgtt tgaggacgac ttgcggcgct agtgatca                 348

<210> SEQ ID NO 3
<211> LENGTH: 636
<212> TYPE: DNA
<213> ORGANISM: Homo sapiens

<400> SEQUENCE: 3
atggcctccc tgttctctgg ccgcatcctg atccgcaaca atagcgacca ggacgagctg     60
gatacggagg ctgaggtcag tcgcaggctg gagaaccggc tggtgctgct gttctttggt    120
```

```
gctgggcctt gtccacagtg ccaggccttc gtgcccatcc tcaaggactt cttcgtgcgg    180
ctcacagatg agttctatgt actgcgggcg gctcagctgg ccctggtgta cgtgtcccag    240
gactccacgg aggagcagca ggacctgttc ctcaaggaca tgccaaagaa atggcttttc    300
ctgccctttg aggatgatct gaggagggac ctcgggcgcc agttctcagt ggagcgcctg    360
ccggcggtcg tggtgctcaa gccggacggg gacgtgctca ctcgcgacgg cgccgacgag    420
atccagcgcc tgggcaccgc ctgcttcgcc aactggcagg aggcggccga ggtgctggac    480
cgcaacttcc agctgccaga ggacctggag gaccaggagc acggagcct caccgagtgc    540 ctgcgccgcc acaagtaccg cgtggaaaag gcggcgcgag gcgggcgcga ccccggggga    600
gggggtgggg aggagggcgg ggccgggggg ctgttc                              636
```

```
<210> SEQ ID NO 4
<211> LENGTH: 4837
<212> TYPE: DNA
<213> ORGANISM: Artificial Sequence
<220> FEATURE:
<223> OTHER INFORMATION: rAAV genome with ITRs flanking an expression
      cassette containing RdCVF sequences and promoters
<220> FEATURE:
<221> NAME/KEY: misc_feature
<222> LOCATION: (17)..(146)
<223> OTHER INFORMATION: AAV 5' ITR
<220> FEATURE:
<221> NAME/KEY: promoter
<222> LOCATION: (207)..(1478)
<220> FEATURE:
<221> NAME/KEY: gene
<222> LOCATION: (1479)..(1826)
<223> OTHER INFORMATION: hRdCVF short form codon optimized sequence
<220> FEATURE:
<221> NAME/KEY: polyA_site
<222> LOCATION: (1821)..(2047)
<220> FEATURE:
<221> NAME/KEY: terminator
<222> LOCATION: (2042)..(2479)
<220> FEATURE:
<221> NAME/KEY: promoter
<222> LOCATION: (2474)..(3774)
<220> FEATURE:
<221> NAME/KEY: gene
<222> LOCATION: (3762)..(4426)
<223> OTHER INFORMATION: hRdCVFL long form codon optimized
<220> FEATURE:
<221> NAME/KEY: polyA_signal
<222> LOCATION: (4427)..(4643)
<220> FEATURE:
<221> NAME/KEY: misc_feature
<222> LOCATION: (4691)..(4820)
<223> OTHER INFORMATION: AAV 3' ITR

<400> SEQUENCE: 4
```

```
gtcgacttaa ttaaggctgc gcgctcgctc gctcactgag gccgcccggg caaagcccgg     60
gcgtcgggcg acctttggtc gcccggcctc agtgagcgag cgagcgcgca gagagggagt    120
ggccaactcc atcactaggg gttccttgta gttaatgatt aacccgccat gctacttatc    180
tacgtagcaa gctagctagt tattaatagt aatcaattac ggggtcatta gttcatagcc    240
catatatgga gttccgcgtt acataactta cggtaaatgg cccgcctggc tgaccgccca    300
acgacccccg cccattgacg tcaataatga cgtatgttcc catagtaacg ccaatagga    360 ctttccattg acgtcaatgg gtggagtatt tacggtaaac tgcccacttg gcagtacatc    420
aagtgtatca tatgccaagt acgccccca ttgacgtcaa tgacggtaaa tggcccgcct    480
ggcattatgc ccagtacatg accttatggg actttcctac ttggcagtac atctacgtat    540
```

```
tagtcatcgc tattaacatg gtcgaggtga gccccacgtt ctgcttcact ctccccatct      600
ccccccctc  cccacccca  attttgtatt tatttatttt ttaattattt tgtgcagcga      660
tgggggcggg ggggggggg  gggcgcgcgc caggcggggc gggcgggc   gaggggcggg      720
gcggggcgag gcggagaggt gcggcggcag ccaatcagag cggcgcgctc cgaaagtttc      780
cttttatggc gaggcggcgg cggcggcggc cctataaaaa gcgaagcgcg cggcgggcgg      840
ggagtcgctg cgacgctgcc ttcgcccgt  gccccgctcc gccgccgcct cgcgccgccc      900
gccccggctc tgactgaccg cgttactccc acaggtgagc gggcgggatg agcacggccc      960
ggcttcgggt gcggggctcc gtacggggcg tggcgcgggg ctcgccgtgc cgggcggggg     1020
gtggcggcag gtgggggtgc cggcgggc   ggggccgcct cgggccgggg agggctcggg     1080
ggaggggcgc ggcggccccc ggagcgccgg cggctgtcga ggcgcggcga ccgcagcca      1140
ttgcctttta tggtaatcgt gcgagagggc gcagggactt cctttgtccc aaatctgtgc     1200
ggagccgaaa tctgggaggc gccgccgcac ccctctagc gggcgcgggg cgaagcggtg      1260
cggcgccggc aggaaggaaa tgggcgggga gggccttcgt gcgtcgccgc gccgccgtcc     1320
ccttctccct ctccagcctc ggggctgtcc gcgggggac ggctgccttc ggggggacg      1380
gggcagggcg gggttcggct tctggcgtgt gaccggcggc tctagacaat tgtactaacc     1440
ttcttctctt tcctctcctg acaggttggt gtacactagc ggccgccacc atggccagcc     1500
tcttctccgg acgcatcctg attcgcaaca attccgacca agacgaactg gataccgagg     1560
ccgaagtctc gcggagattg gagaacaggc ttgtgctgct gttctttggc gcgggagcgt     1620
gtcctcagtg ccaggctttc gtgccaatcc tgaaggattt cttcgtgcgg ctgactgacg     1680
aattctacgt cctccgggcc gcccagctgg cactggtgta cgtgtcccaa gactcaaccg     1740
aggaacagca ggatcgttc  ctcaaggaca tgcccaaaaa gtggctgttc ctgccgtttg     1800
aggacgactt gcggcgctag tgatcagcct cgactgtgcc ttctagttgc cagccatctg     1860
ttgtttgccc ctcccccgtg ccttccttga ccctggaagg tgccactccc actgtcctt      1920
cctaataaaa tgaggaaatt gcatcgcatt gtctgagtag gtgtcattct attctggggg     1980
gtggggtggg gcaggacagc aagggggagg attgggaaga caatagcagg catgctgggg     2040
aggatccaat ttattctaaa tgcataataa atactgataa catcttatag tttgtattat     2100
attttgtatt atcgttgaca tgtataattt tgatatcaaa aactgatttt cctttatta     2160
ttttcgagat ttattttctt aattctcttt aacaaactag aaatattgta tatacaaaaa     2220
atcataaata atagatgaat agtttaatta taggtgttca tcaatcgaaa agcaacgta      2280
tcttatttaa agtgcgttgc ttttttctca tttataaggt taaataattc tcatatatca     2340
agcaaagtga caggcgccct taaatattct gacaaatgct cttccctaa  actcccccca     2400
taaaaaaacc cgccgaagcg ggttttacg  ttatttgcgg attaacgatt actcgttatc     2460
agaaccgccc aggaagcttt agttattaat agtaatcaat tacggggtca ttagttcata     2520
gcccatatat ggagttccgc gttacataac ttacggtaaa tggcccgcct ggctgaccgc     2580
ccaacgaccc ccgcccattg acgtcaataa tgacgtatgt tcccatagta acgccaatag     2640
ggactttcca ttgacgtcaa tgggtggagt atttacggta aactgcccac ttggcagtac     2700
atcaagtgta tcatatgcca agtacgcccc ctattgacgt caatgacggt aaatggcccg     2760
cctggcatta tgcccagtac atgaccttat gggactttcc tacttggcag tacatctacg     2820
tattagtcat cgctattaac atggtcgagg tgagccccac gttctgcttc actctccccca    2880
tctccccccc ctccccaccc ccaattttgt atttatttat tttttaatta ttttgtgcag    2940
```

```
cgatggggc gggggggggg gggggcgcg cgccaggcgg ggcggggcgg ggcgagggc      3000
ggggcgggc gaggcggaga ggtgcggcgg cagccaatca gagcggcgcg ctccgaaagt      3060
ttcctttat ggcgaggcgg cggcggcggc ggccctataa aaagcgaagc gcgcggcggg      3120
cggggagtcg ctgcgacgct gccttcgccc cgtgccccgc tccgccgccg cctcgcgccg      3180
cccgccccgg ctctgactga ccgcgttact cccacaggtg agcgggcggg atgagcacgg      3240
cccggcttcg ggtgcgggc tccgtacggg gcgtggcgcg gggctcgccg tgccgggcgg      3300
ggggtggcgg caggtggggg tgccgggcgg ggcggggccg cctcgggccg ggagggctc      3360
gggggagggg cgcggcggcc cccggagcgc cggcggctgt cgaggcgcgg cgagccgcag      3420
ccattgcctt ttatggtaat cgtgcgagag ggcgcaggga cttcctttgt cccaaatctg      3480
tgcggagccg aaatctggga ggcgccgccg caccccctct agcgggcgcg gggcgaagcg      3540
gtgcggcgcc ggcaggaagg aaatgggcgg ggagggcctt cgtgcgtcgc cgcgccgccg      3600
tccccttctc cctctccagc ctcggggctg tccgcggggg gacggctgcc ttcgggggg      3660
acggggcagg gcggggttcg gcttctggcg tgtgaccggc ggctctagac aattgtacta      3720
accttcttct ctttcctctc ctgacaggtt ggtgtacact aggccataca ggccgccacc      3780
atggcctcac tgttctccgg gcgcatcctc atccgaaaca acagcgatca ggacgaattg      3840
gacaccgagg ctgaagtctc ccgccggctg gaaaacaggc tcgtgctcct gttcttcggt      3900
gccggagcgt gcccgcagtg ccaagccttc gtcccaattc ttaaggactt ctttgtgcgc      3960
ctcactgatg agttttacgt gctccgggca gcgcagctgg ccttggtgta tgtgtcgcaa      4020
gattccactg aggaacaaca ggacctgttc ctgaaagaca tgcctaagaa gtggcttttc      4080
ctgcccttcg aggacgacct gagaagggac ctgggacgcc agttcagcgt ggaacggctg      4140
ccggccgtcg tggtgctgaa gcccgacggg gacgtgctta cccgggatgg cgctgacgaa      4200
atccagaggc tgggcaccgc ctgtttcgca aattggcagg aggccgccga agtgctcgac      4260
cggaacttcc agctgcccga ggatctggag gaccaggaac ctcggtccct gaccgagtgc      4320
ctcagacgcc acaagtaccg cgtggaaaag gccgcgagag gaggacggga cccgggtggc      4380
ggggggaggcg aagagggcgg agccggtggc ctgttctgat agatctgcct cgactgtgcc      4440
ttctagttgc cagccatctg ttgtttgccc ctcccccgtg ccttccttga ccctggaagg      4500
tgccactccc actgtccttt cctaataaaa tgaggaaatt gcatcgcatt gtctgagtag      4560
gtgtcattct attctggggg gtggggtggg gcaggacagc aaggggagg attgggaaga      4620
caatagcagg catgctgggg actcgagttc tacgtagata agtagcatgg cgggttaatc      4680
attaactaca aggaaccct agtgatggag ttggccactc cctctctgcg cgctcgctcg      4740
ctcactgagg ccgggcgacc aaaggtcgcc cgacgcccgg gctttgcccg ggcggcctca      4800
gtgagcgagc gagcgcgcag ccttaattaa cctaagg                              4837
```

<210> SEQ ID NO 5
<211> LENGTH: 4745
<212> TYPE: DNA
<213> ORGANISM: Artificial Sequence
<220> FEATURE:
<223> OTHER INFORMATION: rAAV genome with copies of native hRdCVF and
      promoters
<220> FEATURE:
<221> NAME/KEY: misc_feature
<222> LOCATION: (9)..(100)
<223> OTHER INFORMATION: KanR complement
<220> FEATURE:
<221> NAME/KEY: misc_feature

```
<222> LOCATION: (117)..(246)
<223> OTHER INFORMATION: AAV 5' ITR
<220> FEATURE:
<221> NAME/KEY: promoter
<222> LOCATION: (307)..(1578)
<220> FEATURE:
<221> NAME/KEY: gene
<222> LOCATION: (1591)..(1935)
<223> OTHER INFORMATION: human RdCVF native short form
<220> FEATURE:
<221> NAME/KEY: polyA_signal
<222> LOCATION: (1940)..(2161)
<220> FEATURE:
<221> NAME/KEY: terminator
<222> LOCATION: (2246)..(2546)
<220> FEATURE:
<221> NAME/KEY: misc_feature
<222> LOCATION: (2337)..(2362)
<223> OTHER INFORMATION: pTF3 complement
<220> FEATURE:
<221> NAME/KEY: terminator
<222> LOCATION: (2553)..(2666)
<220> FEATURE:
<221> NAME/KEY: promoter
<222> LOCATION: (2697)..(3968)
<220> FEATURE:
<221> NAME/KEY: gene
<222> LOCATION: (3981)..(4325)
<223> OTHER INFORMATION: hRDCVF native short form second copy
<220> FEATURE:
<221> NAME/KEY: polyA_signal
<222> LOCATION: (4330)..(4551)
<220> FEATURE:
<221> NAME/KEY: misc_feature
<222> LOCATION: (4599)..(4728)
<223> OTHER INFORMATION: AAV 3' ITR

<400> SEQUENCE: 5
tagaaaaact catcgagcat caaatgaaac tgcaatttat tcatatcagg attatcaata      60
ccatattttt gaaaaagccg tttctgtaat gaaggagaaa gtcgacttaa ttaaggctgc     120
gcgctcgctc gctcactgag gccgcccggg caaagcccgg gcgtcgggcg acctttggtc     180
gcccggcctc agtgagcgag cgagcgcgca gagagggagt ggccaactcc atcactaggg     240
gttccttgta gttaatgatt aacccgccat gctacttatc tacgtagcaa gctagctagt     300
tattaatagt aatcaattac ggggtcatta gttcatagcc catatatgga gttccgcgtt     360
acataactta cggtaaatgg cccgcctggc tgaccgccca acgacccccg cccattgacg     420
tcaataatga cgtatgttcc catagtaacg ccaataggga cttccattg acgtcaatgg      480 gtggagtatt tacggtaaac tgcccacttg gcagtacatc aagtgtatca tatgccaagt     540
acgcccccta ttgacgtcaa tgacggtaaa tggcccgcct ggcattatgc ccagtacatg     600
accttatggg actttcctac ttggcagtac atctacgtat tagtcatcgc tattaacatg     660
gtcgaggtga gccccacgtt ctgcttcact ctccccatct cccccccctc cccacccca      720 attttgtatt tatttatttt ttaattattt tgtgcagcga tgggggcggg ggggggggg      780 gggcgcgcgc caggcgggc ggggcgggc gaggggcggg gcgggcgag gcggagaggt     840 gcggcggcag ccaatcagag cggcgcgctc cgaaagtttc cttttatggc gaggcggcgg      900
cggcggcggc cctataaaaa gcgaagcgcg cggcgggcgg ggagtcgctg cgacgctgcc      960
ttcgccccgt gccccgctcc gccgccgcct cgcgccgccc gccccggctc tgactgaccg     1020
cgttactccc acaggtgagc gggcgggatg agcacggccc ggcttcgggt gcggggctcc     1080
gtacggggcg tggcgcgggg ctcgccgtgc cgggcggggg gtggcggcag gtggggtgc      1140 cgggcggggc ggggccgcct cgggccgggg agggctcggg ggaggggcgc ggcggccccc     1200
```

-continued

```
ggagcgccgg cggctgtcga ggcgcggcga gccgcagcca ttgccttttta tggtaatcgt    1260 gcgagagggc gcagggactt cctttgtccc aaatctgtgc ggagccgaaa tctgggaggc    1320
gccgccgcac cccctctagc gggcgcgggg cgaagcggtg cggcgccggc aggaaggaaa    1380 tgggcggggga gggccttcgt gcgtcgccgc ccgccgtcc ccttctccct ctccagcctc    1440
ggggctgtcc gcggggggac ggctgccttc ggggggacg gggcagggcg gggttcggct    1500
tctggcgtgt gaccggcggc tctagacaat tgtactaacc ttcttctctt tcctctcctg    1560
acaggttggt gtacactagc ggccgccacc atggcctccc tgttctctgg ccgcatcctg    1620
atccgcaaca atagcgacca ggacgagctg gatacgagg ctgaggtcag tcgcaggctg    1680
gagaaccggc tggtgctgct gttctttggt gctggggctt gtccacagtg ccaggccttc    1740
gtgcccatcc tcaaggactt cttcgtgcgg ctcacagatg agttctatgt actgcgggcg    1800
gctcagctgg ccctggtgta cgtgtcccag gactccacgg aggagcagca ggacctgttc    1860
ctcaaggaca tgccaaagaa atggcttttc ctgcccttg aggatgatct gaggaggtga    1920
tcatctcatg gatccaagag atctgcctcg actgtgcctt ctagttgcca gccatctgtt    1980
gtttgcccct cccccgtgcc ttccttgacc ctggaaggtg ccactcccac tgtcctttcc    2040
taataaaatg aggaaattgc atcgcattgt ctgagtaggt gtcattctat tctgggggt    2100 ggggtggggc aggacagcaa gggggaggat tgggaagaca atagcaggca tgctggggac    2160
tcgataagga aaatgaagtg aagttcctat actttctaga gaataggaac ttctatagtg    2220
agtcgaataa gggcgacaca aaatttattc taaatgcata ataaatactg ataacatctt    2280
atagtttgta ttatatttg tattatcgtt gacatgtata atttgatat caaaaactga    2340 ttttcccttt attattttcg agatttattt tcttaattct ctttaacaaa ctagaaatat    2400
tgtatataca aaaaatcata aataatagat gaatagttta attataggtg ttcatcaatc    2460
gaaaaagcaa cgtatcttat ttaaagtgcg ttgcttttt ctcatttata aggttaaata    2520
attctcatat atcaagcaaa gtgacaggcg cccttaaata ttctgacaaa tgctctttcc    2580
ctaaactccc cccataaaaa aacccgccga agcgggtttt tacgttattt gcggattaac    2640
gattactcgt tatcagaacc gcccaggggg cccgagctta actagctagt tattaatagt    2700
aatcaattac ggggtcatta gttcatagcc catatatgga gttccgcgtt acataactta    2760
cggtaaatgg cccgcctggc tgaccgccca acgacccccg cccattgacg tcaataatga    2820
cgtatgttcc catagtaacg ccaatagga cttttccattg acgtcaatgg gtggagtatt    2880
tacggtaaac tgcccacttg gcagtacatc aagtgtatca tatgccaagt acgccccta    2940 ttgacgtcaa tgacggtaaa tggcccgcct ggcattatgc ccagtacatg accttatggg    3000
actttcctac ttggcagtac atctacgtat tagtcatcgc tattaacatg gtcgaggtga    3060
gccccacgtt ctgcttcact ctccccatct ccccccctc cccaccccca attttgtatt    3120
tatttatttt ttaattattt tgtgcagcga tgggggcggg ggggggggg gggcgcgcgc    3180 caggcggggc gggcgggc gagggcggg gcggggcgag gcgagaggt gcggcggcag    3240 ccaatcagag cggcgcgctc cgaaagtttc cttttatggc gaggcggcgg cggcggcggc    3300
cctataaaaa gcgaagcgcg cggcgggcgg ggagtcgctg cgacgctgcc ttcgccccgt    3360
gccccgctcc gccgccgcct cgcgccgccc gccccggctc tgactgaccg cgttactccc    3420
acaggtgagc gggcgggatg agcacggccc ggcttcgggt gcgggctcc gtacggggcg    3480 tggcgcgggg ctcgccgtgc cgggcggggg gtggcggcag gtgggggtgc cgggcgggc    3540 ggggccgcct cgggccgggg agggctcggg ggaggggcgc ggcggccccc ggagcgccgg    3600
```

```
cggctgtcga ggcgcggcga gccgcagcca ttgcctttta tggtaatcgt gcgagagggc    3660
gcagggactt cctttgtccc aaatctgtgc ggagccgaaa tctgggaggc gccgccgcac    3720
cccctctagc gggcgcgggg cgaagcggtg cggcgccggc aggaaggaaa tgggcgggga    3780
gggccttcgt gcgtcgccgc gccgccgtcc ccttctccct ctccagcctc ggggctgtcc    3840
gcggggggac ggctgccttc ggggggacg gggcagggcg gggttcggct tctggcgtgt    3900
gaccggcggc tctagacaat tgtactaacc ttcttctctt tcctctcctg acaggttggt    3960
gtacactagc ggccgccacc atggcctccc tgttctctgg ccgcatcctg atccgcaaca    4020
atagcgacca ggacgagctg gatacggagg ctgaggtcag tcgcaggctg gagaaccggc    4080
tggtgctgct gttctttggt gctggggctt gtccacagtg ccaggccttc gtgcccatcc    4140
tcaaggactt cttcgtgcgg ctcacagatg agttctatgt actgcgggcg gctcagctgg    4200
ccctggtgta cgtgtcccag gactccacgg aggagcagca ggacctgttc ctcaaggaca    4260
tgccaaagaa atggcttttc ctgccctttg aggatgatct gaggaggtga tcatctcatg    4320
gatccaagag atctgcctcg actgtgcctt ctagttgcca gccatctgtt gtttgcccct    4380
cccccgtgcc ttccttgacc ctggaaggtg ccactcccac tgtcctttcc taataaaatg    4440
aggaaattgc atcgcattgt ctgagtaggt gtcattctat tctgggggt ggggtggggc    4500 aggacagcaa gggggaggat tgggaagaca atagcaggca tgctggggac tcgagttcta    4560
cgtagataag tagcatggcg ggttaatcat taactacaag gaacccctag tgatggagtt    4620
ggccactccc tctctgcgcg ctcgctcgct cactgaggcc gggcgaccaa aggtcgcccg    4680
acgcccgggc tttgcccggg cggcctcagt gagcgagcga gcgcgcagcc ttaattaacc    4740
taagg                                                                4745
```

<210> SEQ ID NO 6
<211> LENGTH: 12464
<212> TYPE: DNA
<213> ORGANISM: Artificial Sequence
<220> FEATURE:
<223> OTHER INFORMATION: Plasmid containing the p857 rAAV genome
      containing native 2xRdCVF
<220> FEATURE:
<221> NAME/KEY: misc_feature
<222> LOCATION: (9)..(903)
<223> OTHER INFORMATION: KanR complement
<220> FEATURE:
<221> NAME/KEY: misc_feature
<222> LOCATION: (988)..(1162)
<223> OTHER INFORMATION: B1 B2 T1 Txn Terminator Complement
<220> FEATURE:
<221> NAME/KEY: misc_feature
<222> LOCATION: (1063)..(1079)
<223> OTHER INFORMATION: pTR
<220> FEATURE:
<221> NAME/KEY: misc_feature
<222> LOCATION: (1253)..(1382 )
<223> OTHER INFORMATION: AAV 5 ITR
<220> FEATURE:
<221> NAME/KEY: promoter
<222> LOCATION: (1443)..(2714)
<220> FEATURE:
<221> NAME/KEY: gene
<222> LOCATION: (2727)..(3071)
<223> OTHER INFORMATION: hRdCVF (native short form)
<220> FEATURE:
<221> NAME/KEY: polyA_signal
<222> LOCATION: (3076)..(3297)
<220> FEATURE:
<221> NAME/KEY: terminator
<222> LOCATION: (3382)..(3682)
<220> FEATURE:

```
<221> NAME/KEY: misc_feature
<222> LOCATION: (3473)..(3498)
<223> OTHER INFORMATION: pTF3 complement
<220> FEATURE:
<221> NAME/KEY: terminator
<222> LOCATION: (3689)..(3802)
<220> FEATURE:
<221> NAME/KEY: promoter
<222> LOCATION: (3833)..(5104)
<220> FEATURE:
<221> NAME/KEY: gene
<222> LOCATION: (5117)..(5461)
<223> OTHER INFORMATION: hRdCVF native short form second copy
<220> FEATURE:
<221> NAME/KEY: polyA_signal
<222> LOCATION: (5466)..(5687)
<220> FEATURE:
<221> NAME/KEY: misc_feature
<222> LOCATION: (5735)..(5864)
<223> OTHER INFORMATION: AAV 3' ITR
<220> FEATURE:
<221> NAME/KEY: terminator
<222> LOCATION: (5958)..(6258)
<220> FEATURE:
<221> NAME/KEY: misc_feature
<222> LOCATION: (6049)..(6074)
<223> OTHER INFORMATION: pTF3 Complement
<220> FEATURE:
<221> NAME/KEY: terminator
<222> LOCATION: (6265)..(6378)
<220> FEATURE:
<221> NAME/KEY: misc_feature
<222> LOCATION: (6394)..(11460)
<223> OTHER INFORMATION: Lambda Stuffer
<220> FEATURE:
<221> NAME/KEY: misc_feature
<222> LOCATION: (11621)..(12424)
<223> OTHER INFORMATION: pUC Ori Complement

<400> SEQUENCE: 6
tagaaaaact catcgagcat caaatgaaac tgcaatttat tcatatcagg attatcaata      60 ccatatttt  gaaaaagccg tttctgtaat gaaggagaaa actcaccgag gcagttccat     120
aggatggcaa gatcctggta tcggtctgcg attccgactc gtccaacatc aatacaacct    180
attaatttcc cctcgtcaaa aataaggtta tcaagtgaga atcaccatg agtgacgact     240 gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020 tgacccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
```

```
gggcctttcg cccgggctaa ttaggggtg tcgcccttat tcgactctat agtgaagttc    1200
ctattctcta gaaagtatag gaacttctga agtggggtcg acttaattaa ggctgcgcgc   1260
tcgctcgctc actgaggccg cccgggcaaa gcccggcgt cgggcgacct ttggtcgccc    1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc ccctccca ccccaattt      1860
tgtatttatt tattttttaa ttattttgtg cagcgatggg ggcggggggg ggggggggc   1920
gcgcgccagg cggggcgggg cgggggcgagg ggcggggcgg ggcgaggcgg agaggtgcgg  1980
cggcagccaa tcagagcggc gcgctccgaa agtttccttt tatggcgagg cggcggcggc   2040
ggcggcccta taaaagcga agcgcgcggc gggcggggag tcgctgcgac gctgccttcg    2100
ccccgtgccc cgctccgccg ccgcctcgcg ccgcccgccc cggctctgac tgaccgcgtt   2160
actcccacag gtgagcgggc gggatgagca cggcccggct tcgggtgcgg ggctccgtac   2220
ggggcgtggc gcggggctcg ccgtgccggg cgggggggtgg cggcaggtgg gggtgccggg  2280
cggggcgggg ccgcctcggg ccggggaggg ctcggggag gggcgcggcg gcccccggag    2340
cgccggcggc tgtcgaggcg cggcgagccg cagccattgc cttttatggt aatcgtgcga   2400
gagggcgcag ggacttcctt tgtcccaaat ctgtgcggag ccgaaatctg ggaggcgccg   2460
ccgcaccccc tctagcgggc gcggggcgaa gcggtgcggc gccggcagga aggaaatggg   2520
cggggagggc cttcgtgcgt cgccgcgccg ccgtcccctt ctccctctcc agcctcgggg   2580
ctgtccgcgg gggacggct gccttcgggg gggacggggc agggcggggt tcggcttctg    2640
gcgtgtgacc ggcggctcta gacaattgta ctaaccttct tctctttcct ctcctgacag   2700
gttggtgtac actagcggcc gccaccatgg cctcccctgtt ctctggccgc atcctgatcc   2760
gcaacaatag cgaccaggac gagctggata cggaggctga ggtcagtcgc aggctggaga   2820
accggctggt gctgctgttc tttggtgctg gggcttgtcc acagtgccag gccttcgtgc   2880
ccatcctcaa ggacttcttc gtgcggctca cagatgagtt ctatgtactg cgggcggctc   2940
agctggccct ggtgtacgtg tcccaggact ccacggagga gcagcaggac ctgttcctca   3000
aggacatgcc aaagaaatgg cttttcctgc cctttgagga tgatctgagg aggtgatcat   3060
ctcatggatc caagagatct gcctcgactg tgccttctag ttgccagcca tctgttgttt   3120
gcccctcccc cgtgccttcc ttgaccctgg aaggtgccac tcccactgtc ctttcctaat   3180
aaaatgagga aattgcatcg cattgtctga gtaggtgtca ttctattctg gggggtgggg   3240
tggggcagga cagcaagggg gaggattggg aagacaatag caggcatgct ggggactcga   3300
taaggaaaat gaagtgaagt tcctatactt tctagagaat aggaacttct atagtgagtc   3360
gaataagggc gacacaaaat ttattctaaa tgcataataa atactgataa catcttatag   3420
tttgtattat attttgtatt atcgttgaca tgtataattt tgatatcaaa aactgatttt   3480
ccctttatta ttttcgagat ttattttctt aattctcttt aacaaactag aaatattgta   3540
```

```
tatacaaaaa atcataaata atagatgaat agtttaatta taggtgttca tcaatcgaaa    3600
aagcaacgta tcttatttaa agtgcgttgc ttttttctca tttataaggt taaataattc    3660
tcatatatca agcaaagtga caggcgccct taaatattct gacaaatgct ctttccctaa    3720
actcccccca taaaaaaacc cgccgaagcg ggtttttacg ttatttgcgg attaacgatt    3780
actcgttatc agaaccgccc aggggggcccg agcttaacta gctagttatt aatagtaatc    3840
aattacgggg tcattagttc atagcccata tatggagttc cgcgttacat aacttacggt    3900
aaatggcccg cctggctgac cgcccaacga ccccgccca ttgacgtcaa taatgacgta    3960
tgttcccata gtaacgccaa tagggacttt ccattgacgt caatgggtgg agtatttacg    4020
gtaaactgcc cacttggcag tacatcaagt gtatcatatg ccaagtacgc ccctattga    4080
cgtcaatgac ggtaaatggc ccgcctggca ttatgcccag tacatgacct tatgggactt    4140
tcctacttgg cagtacatct acgtattagt catcgctatt aacatggtcg aggtgagccc    4200
cacgttctgc ttcactctcc ccatctcccc ccctcccca ccccaattt tgtatttatt    4260
tatttttaa ttattttgtg cagcgatggg ggcggggggg gggggggggc gcgcgccagg    4320
cggggcgggg cggggcgagg ggcgggggcgg ggcgaggcgg agaggtgcgg cggcagccaa    4380
tcagagcggc gcgctccgaa agtttccttt tatggcgagg cggcggcggc ggcggcccta    4440
taaaaagcga agcgcgcggc gggcggggag tcgctgcgac gctgccttcg ccccgtgccc    4500
cgctccgccg ccgcctcgcg ccgcccgccc cggctctgac tgaccgcgtt actcccacag    4560
gtgagcgggc gggatgagca cggccccggct tcgggtgcgg ggctccgtac ggggcgtggc    4620
gcggggctcg ccgtgccggg cggggggtgg cggcaggtgg gggtgccggg cggggcgggg    4680
ccgcctcggg ccggggaggg ctcggggggag gggcgcggcg gccccggag cgccggcggc    4740
tgtcgaggcg cggcgagccg cagccattgc ctttttatggt aatcgtgcga gagggcgcag    4800
ggacttcctt tgtcccaaat ctgtgcggag ccgaaatctg ggaggcgccg ccgcaccccc    4860
tctagcgggc gcggggcgaa gcggtgcggc gccggcagga aggaaatggg cggggagggc    4920
cttcgtgcgt cgccgcgccg ccgtcccctt ctccctctcc agcctcgggg ctgtccgcgg    4980
ggggacggct gccttcgggg gggacggggc agggcggggt tcggcttctg gcgtgtgacc    5040
ggcggctcta gacaattgta ctaaccttct tctctttcct ctcctgacag gttggtgtac    5100
actagcggcc gccaccatgg cctccctgtt tctggccgc atcctgatcc gcaacaatag    5160
cgaccaggac gagctggata cggaggctga ggtcagtcgc aggctggaga accggctggt    5220
gctgctgttc tttggtgctg gggcttgtcc acagtgccag gccttcgtgc ccatcctcaa    5280
ggacttcttc gtgcggctca cagatgagtt ctatgtactg cgggcggctc agctggccct    5340
ggtgtacgtg tccaggact ccacggagga gcagcaggac ctgttcctca aggacatgcc    5400
aaagaaatgg cttttcctgc cctttgagga tgatctgagg aggtgatcat ctcatggatc    5460
caagagatct gcctcgactg tgccttctag ttgccagcca tctgttgttt gcccctcccc    5520
cgtgccttcc ttgaccctgg aaggtgccac tcccactgtc ctttcctaat aaaatgagga    5580
aattgcatcg cattgtctga gtaggtgtca ttctattctg gggggtgggg tgggcagga    5640
cagcaagggg gaggattggg aagacaatag caggcatgct ggggactcga gttctacgta    5700
gataagtagc atggcgggtt aatcattaac tacaaggaac cctagtgat ggagttggcc    5760
actccctctc tgcgcgctcg ctcgctcact gaggccgggc gaccaaaggt cgcccgacgc    5820
ccgggctttg cccgggcggc ctcagtgagc gagcgagcgc gcagccttaa ttaacctaag    5880
```

```
gaaaatgaag tgaagttcct atactttcta gagaatagga acttctatag tgagtcgaat    5940
aagggcgaca caaaatttat tctaaatgca taataaatac tgataacatc ttatagtttg    6000
tattatattt tgtattatcg ttgacatgta taattttgat atcaaaaact gattttccct    6060
ttattatttt cgagatttat tttcttaatt ctctttaaca aactagaaat attgtatata    6120
caaaaaatca taaataatag atgaatagtt taattatagg tgttcatcaa tcgaaaaagc    6180
aacgtatctt atttaaagtg cgttgctttt ttctcattta taaggttaaa taattctcat    6240
atatcaagca aagtgacagg cgcccttaaa tattctgaca aatgctcttt ccctaaactc    6300
cccccataaa aaaacccgcc gaagcgggtt tttacgttat ttgcggatta acgattactc    6360
gttatcagaa ccgcccaggg ggcccgagct taaccttttt atttggggga gagggaagtc    6420
atgaaaaaac taacctttga aattcgatct ccagcacatc agcaaaacgc tattcacgca    6480
gtacagcaaa tccttccaga cccaaccaaa ccaatcgtag taaccattca ggaacgcaac    6540
cgcagcttag accaaaacag gaagctatgg gcctgcttag gtgacgtctc tcgtcaggtt    6600
gaatggcatg gtcgctggct ggatgcagaa agctggaagt gtgtgtttac cgcagcatta    6660
aagcagcagg atgttgttcc taaccttgcc gggaatggct ttgtggtaat aggccagtca    6720
accagcagga tgcgtgtagg cgaatttgcg gagctattag agcttataca ggcattcggt    6780
acagagcgtg gcgttaagtg gtcagacgaa gcgagactgg ctctggagtg gaaagcgaga    6840
tggggagaca gggctgcatg ataaatgtcg ttagtttctc cggtggcagg acgtcagcat    6900
atttgctctg gctaatggag caaaagcgac gggcaggtaa agacgtgcat tacgttttca    6960
tggatacagg ttgtgaacat ccaatgacat atcggtttgt cagggaagtt gtgaagttct    7020
gggatatacc gctcaccgta ttgcaggttg atatcaaccc ggagcttgga cagccaaatg    7080
gttatacggt atgggaacca aaggatattc agacgcgaat gcctgttctg aagccattta    7140
tcgatatggt aaagaaatat ggcactccat acgtcggcgg cgcgttctgc actgacagat    7200
taaaactcgt tcccttcacc aaatactgtg atgaccattt cgggcgaggg aattacacca    7260
cgtggattgg catcagagct gatgaaccga agcggctaaa gccaaagcct ggaatcagat    7320
atcttgctga actgtcagac tttgagaagg aagatatcct cgcatggtgg aagcaacaac    7380
cattcgattt gcaaataccg gaacatctcg gtaactgcat attctgcatt aaaaaatcaa    7440
cgcaaaaaat cggacttgcc tgcaaagatg aggagggatt gcagcgtgtt tttaatgagg    7500
tcatcacggg atcccatgtg cgtgacggac atcgggaaac gccaaaggag attatgtacc    7560
gaggaagaat gtcgctggac ggtatcgcga aaatgtattc agaaaatgat tatcaagccc    7620
tgtatcagga catggtacga gctaaaagat tcgataccgg ctcttgttct gagtcatgcg    7680
aaatatttgg agggcagctt gatttcgact tcgggaggga agctgcatga tgcgatgtta    7740
tcggtgcggt gaatgcaaag aagataaccg cttccgacca aatcaacctt actggaatcg    7800
atggtgtctc cggtgtgaaa gaacaccaac agggtgtta ccactaccgc aggaaaagga    7860
ggacgtgtgg cgagacagcg acgaagtatc accgacataa tctgcgaaaa ctgcaaatac    7920
cttccaacga aacgcaccag aaataaaccc aagccaatcc caaagaatc tgacgtaaaa    7980 accttcaact cacacggctca cctgtgggat atccggtggc taagacgtcg tgcgaggaaa    8040
acaaggtgat tgaccaaaat cgaagttacg aacaagaaag cgtcgagcga gctttaacgt    8100
gcgctaactg cggtcagaag ctgcatgtgc tggaagttca cgtgtgtgag cactgctgcg    8160
cagaactgat gagcgatccg aatagctcga tgcacgagga agaagatgat ggctaaacca    8220
gcgcgaagac gatgtaaaaa cgatgaatgc cgggaatggt ttcaccctgc attcgctaat    8280
```

```
cagtggtggt gctctccaga gtgtggaacc aagatagcac tcgaacgacg aagtaaagaa    8340
cgcgaaaaag cggaaaaagc agcagagaag aaacgacgac gagaggagca gaaacagaaa    8400
gataaactta agattcgaaa actcgcctta agccccgca gttactggat taaacaagcc     8460
caacaagccg taaacgcctt catcagagaa agagaccgcg acttaccatg tatctcgtgc    8520
ggaacgctca cgtctgctca gtgggatgcc ggacattacc ggacaactgc tgcggcacct    8580
caactccgat ttaatgaacg caatattcac aagcaatgcg tggtgtgcaa ccagcacaaa    8640
agcggaaatc tcgttccgta tcgcgtcgaa ctgattagcc gcatcgggca ggaagcagta    8700
gacgaaatcg aatcaaacca taaccgccat cgctggacta tcgaagagtg caaggcgatc    8760
aaggcagagt accaacagaa actcaaagac ctgcgaaata gcagaagtga ggccgcatga    8820
cgttctcagt aaaaaccatt ccagacatgc tcgttgaagc atacgaaat cagacagaag     8880 tagcacgcag actgaaatgt agtcgcggta cggtcagaaa atacgttgat gataaagacg    8940
ggaaaatgca cgccatcgtc aacgacgttc tcatggttca tcgcggatgg agtgaaagag    9000
atgcgctatt acgaaaaaat tgatggcagc aaataccgaa atatttgggt agttggcgat    9060
ctgcacggat gctacacgaa cctgatgaac aaactggata cgattggatt cgacaacaaa    9120
aaagacctgc ttatctcggt gggcgatttg gttgatcgtg gtgcagagaa cgttgaatgc    9180
ctggaattaa tcacattccc ctggttcaga gctgtacgtg gaaaccatga gcaaatgatg    9240
attgatggct tatcagagcg tggaaacgtt aatcactggc tgcttaatgg cggtggctgg    9300
ttctttaatc tcgattacga caaagaaatt ctggctaaag ctcttgccca taaagcagat    9360
gaacttccgt taatcatcga actggtgagc aaagataaaa aatatgttat ctgccacgcc    9420
gattatccct ttgacgaata cgagtttgga aagccagttg atcatcagca ggtaatctgg    9480
aaccgcgaac gaatcagcaa ctcacaaaac gggatcgtga agaaatcaa aggcgcggac     9540 acgttcatct ttggtcatac gccagcagtg aaaccactca gtttgccaa ccaaatgtat     9600 atcgataccg gcgcagtgtt ctgcggaaac ctaacattga ttcaggtaca gggagaaggc    9660
gcatgagact cgaaagcgta gctaaatttc attcgccaaa aagcccgatg atgagcgact    9720
caccacgggc cacggcttct gactctcttt ccggtactga tgtgatggct gctatgggga    9780
tggcgcaatc acaagccgga ttcggtatgg ctgcattctg cggtaagcac gaactcagcc    9840
agaacgacaa acaaaaggct atcaactatc tgatgcaatt tgcacacaag gtatcgggga    9900
aataccgtgg tgtggcaaag cttgaaggaa atactaaggc aaaggtactg caagtgctcg    9960
caacattcgc ttatgcggat tattgccgta gtgccgcgac gccggggca agatgcagag    10020 attgccatgg tacaggccgt gcggttgata ttgccaaaac agagctgtgg gggagagttg   10080
tcgagaaaga gtgcggaaga tgcaaaggcg tcggctattc aaggatgcca gcaagcgcag   10140
catatcgcgc tgtgacgatg ctaatcccaa accttaccca acccacctgg tcacgcactg   10200
ttaagccgct gtatgacgct ctggtggtgc aatgccacaa agaagagtca atcgcagaca   10260
acattttgaa tgcggtcaca cgttagcagc atgattgcca cggatggcaa catattaacg   10320
gcatgatatt gacttattga ataaaattgg gtaaatttga ctcaacgatg ggttaattcg   10380
ctcgttgtgg tagtgagatg aaaagaggcg gcgcttacta ccgattccgc ctagttggtc   10440
acttcgacgt atcgtctgga actccaacca tcgcaggcag agaggtctgc aaaatgcaat   10500
cccgaaacag ttcgcaggta atagttagag cctgcataac ggtttcggga ttttttatat   10560
ctgcacaaca ggtaagagca ttgagtcgat aatcgtgaag agtcggcgag cctggttagc   10620
```

```
cagtgctctt tccgttgtgc tgaattaagc gaataccgga agcagaaccg gatcaccaaa    10680
tgcgtacagg cgtcatcgcc gcccagcaac agcacaaccc aaactgagcc gtagccactg    10740
tctgtcctga attcattagt aatagttacg ctgcggcctt ttacacatga ccttcgtgaa    10800
agcgggtggc aggaggtcgc gctaacaacc tcctgccgtt ttgcccgtgc atatcggtca    10860
cgaacaaatc tgattactaa acacagtagc ctggatttgt tctatcagta atcgacctta    10920
ttcctaatta aatagagcaa atccccttat tggggggtaag acatgaagat gccagaaaaa    10980
catgacctgt tggccgccat tctcgcggca aaggaacaag gcatcggggc aatccttgcg    11040
tttgcaatgg cgtaccttcg cggcagatat aatggcggtg cgtttacaaa acagtaatc     11100 gacgcaacga tgtgcgccat tatcgcctgg ttcattcgtg accttctcga cttcgccgga    11160
ctaagtagca atctcgctta tataacgagc gtgtttatcg gctacatcgg tactgactcg    11220
attggttcgc ttatcaaacg cttcgctgct aaaaaagccg gagtagaaga tggtagaaat    11280
caataatcaa cgtaaggcgt tcctcgatat gctggcgtgg tcggagggaa ctgataacgg    11340
acgtcagaaa accagaaatc atggttatga cgtcattgta ggcggagagc tatttactga    11400
ttactccgat caccctcgca aacttgtcac gctaaaccca aaactcaaat caacaggcgc    11460
ttaagactgg ccgtcgtttt acaacacaga agagtttgt agaaacgcaa aaaggccatc     11520
cgtcaggggc cttctgctta gtttgatgcc tggcagttcc ctactctcgc cttccgcttc    11580
ctcgctcact gactcgctgc gctcggtcgt tcggctgcgg cgagcggtat cagctcactc    11640
aaaggcggta atacggttat ccacagaatc aggggataac gcaggaaaga acatgtgagc    11700
aaaaggccag caaaaggcca ggaaccgtaa aaaggccgcg ttgctggcgt ttttccatag    11760
gctccgcccc cctgacgagc atcacaaaaa tcgacgctca agtcagaggt ggcgaaaccc    11820
gacaggacta taaagatacc aggcgtttcc ccctggaagc tccctcgtgc gctctcctgt    11880
tccgaccctg ccgcttaccg gatacctgtc cgcctttctc ccttcgggaa gcgtggcgct    11940
ttctcatagc tcacgctgta ggtatctcag ttcggtgtag gtcgttcgct ccaagctggg    12000
ctgtgtgcac gaaccccccg ttcagcccga ccgctgcgcc ttatccggta actatcgtct    12060
tgagtccaac ccggtaagac acgacttatc gccactggca gcagccactg gtaacaggat    12120
tagcagagcg aggtatgtag gcggtgctac agagttcttg aagtggtggg ctaactacgg    12180
ctacactaga agaacagtat ttggtatctg cgctctgctg aagccagtta ccttcggaaa    12240
aagagttggt agctcttgat ccggcaaaca aaccaccgct ggtagcggtg ttttttttgt    12300
ttgcaagcag cagattacgc gcagaaaaaa aggatctcaa gaagatcctt tgatcttttc    12360
tacggggtct gacgctcagt ggaacgacgc gcgcgtaact cacgttaagg gattttggtc    12420
atgagcttgc gccgtcccgt caagtcagcg taatgctctg cttt                     12464
```

<210> SEQ ID NO 7
<211> LENGTH: 12656
<212> TYPE: DNA
<213> ORGANISM: Artificial Sequence
<220> FEATURE:
<223> OTHER INFORMATION: Plasmid containing the rAAV genome of p853
<220> FEATURE:
<221> NAME/KEY: misc_feature
<222> LOCATION: (9)..(803)
<223> OTHER INFORMATION: KanR Complement
<220> FEATURE:
<221> NAME/KEY: misc_feature
<222> LOCATION: (988)..(1162)
<223> OTHER INFORMATION: B1 B2 T1 Txn Terminator Complement
<220> FEATURE:
<221> NAME/KEY: misc_feature

```
<222> LOCATION: (1063)..(1079)
<223> OTHER INFORMATION: pTR
<220> FEATURE:
<221> NAME/KEY: misc_feature
<222> LOCATION: (1253)..(1382  )
<223> OTHER INFORMATION: AAV 5' ITR
<220> FEATURE:
<221> NAME/KEY: promoter
<222> LOCATION: (1443)..(2714)
<220> FEATURE:
<221> NAME/KEY: gene
<222> LOCATION: (2715 )..(3062)
<223> OTHER INFORMATION: human hRdCVF short form optimized sequence
<220> FEATURE:
<221> NAME/KEY: polyA_signal
<222> LOCATION: (3057 )..(3283)
<220> FEATURE:
<221> NAME/KEY: terminator
<222> LOCATION: (3278 )..(3715)
<220> FEATURE:
<221> NAME/KEY: promoter
<222> LOCATION: (3710)..(5010)
<220> FEATURE:
<221> NAME/KEY: gene
<222> LOCATION: (4998 )..(5662)
<223> OTHER INFORMATION: hRDCVFL optimized sequence long form
<220> FEATURE:
<221> NAME/KEY: polyA_signal
<222> LOCATION: (5663 )..(5879)
<220> FEATURE:
<221> NAME/KEY: misc_feature
<222> LOCATION: (5927)..(6056)
<223> OTHER INFORMATION: AAV 3' ITR
<220> FEATURE:
<221> NAME/KEY: terminator
<222> LOCATION: (6150)..(6450)
<220> FEATURE:
<221> NAME/KEY: misc_feature
<222> LOCATION: (6241)..(6266)
<223> OTHER INFORMATION: pTF3 Complement
<220> FEATURE:
<221> NAME/KEY: terminator
<222> LOCATION: (6457)..(6570)
<220> FEATURE:
<221> NAME/KEY: misc_feature
<222> LOCATION: (6586)..(11652)
<223> OTHER INFORMATION: Lambda Stuffer
<220> FEATURE:
<221> NAME/KEY: misc_feature
<222> LOCATION: (11813)..(12616)
<223> OTHER INFORMATION: pUC Ori Complement

<400> SEQUENCE: 7
tagaaaaact catcgagcat caaatgaaac tgcaatttat tcatatcagg attatcaata      60 ccatatttt  gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa aataaggtta tcaagtgaga atcaccatg agtgacgact      240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgttttccg gggatcgcag tggtgagtaa ccatgcatca      540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccattta ta cccatataaa tcagcatcca tgttggaatt taatcgcggc     780
```

```
ctcgacgttt cccgttgaat atggctcata ttcttccttt ttcaatatta ttgaagcatt      840
tatcagggtt attgtctcat gagcggatac atatttgaat gtatttagaa aaataaacaa      900
ataggggtca gtgttacaac caattaacca attctgaaca ttatcgcgag cccatttata      960
cctgaatatg gctcataaca cccctttgttt gcctggcggc agtagcgcgg tggtcccacc    1020
tgaccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttaggggtg tcgcccttat tcgactctat agtgaagttc    1200
ctattctcta gaaagtatag gaacttctga agtggggtcg acttaattaa ggctgcgcgc    1260
tcgctcgctc actgaggccg cccgggcaaa gcccgggcgt cgggcgacct ttggtcgccc    1320
ggcctcagtg agcgagcgag cgcgcagaga gggagtggcc aactccatca ctaggggttc    1380
cttgtagtta atgattaacc cgccatgcta cttatctacg tagcaagcta gctagttatt    1440
aatagtaatc aattacgggg tcattagttc atagcccata tatggagttc cgcgttacat    1500
aacttacggt aaatggcccg cctggctgac cgcccaacga cccccgccca ttgacgtcaa    1560
taatgacgta tgttcccata gtaacgccaa tagggacttt ccattgacgt caatgggtgg    1620
agtatttacg gtaaactgcc cacttggcag tacatcaagt gtatcatatg ccaagtacgc    1680
cccctattga cgtcaatgac ggtaaatggc ccgcctggca ttatgcccag tacatgacct    1740
tatgggactt tcctacttgg cagtacatct acgtattagt catcgctatt aacatggtcg    1800
aggtgagccc cacgttctgc ttcactctcc ccatctcccc cccctcccca ccccaatttt    1860
tgtatttatt tatttttaa ttatttttgtg cagcgatggg ggcggggggg ggggggggc    1920
gcgcgccagg cggggcgggg cggggcgagg ggcggggcgg ggcgaggcgg agaggtgcgg    1980
cggcagccaa tcagagcggc gcgctccgaa agtttccttt tatggcgagg cggcggcggc    2040
ggcggcccta taaaaagcga agcgcgcggc gggcggggag tcgctgcgac gctgccttcg    2100
ccccgtgccc cgctccgccg ccgcctcgcg ccgcccgccc cggctctgac tgaccgcgtt    2160
actcccacag gtgagcgggc gggatgagca cggcccggct tcgggtgcgg ggctccgtac    2220
ggggcgtggc gcggggctcg ccgtgccggg cggggggtgg cggcaggtgg gggtgccggg    2280
cggggcgggg ccgcctcggg ccggggaggg ctcgggggag gggcgcggcg gcccccggag    2340
cgccggcggc tgtcgaggcg cggcgagccg cagccattgc cttttatggt aatcgtgcga    2400
gagggcgcag ggacttcctt tgtcccaaat ctgtgcggag ccgaaatctg ggaggcgccg    2460
ccgcaccccc tctagcgggc gcggggcgaa gcggtgcggc gccggcagga aggaaatggg    2520
cggggagggc cttcgtgcgt cgccgcgccg ccgtcccctt ctccctctcc agcctcgggg    2580
ctgtccgcgg ggggacggct gccttcgggg gggacgggc agggcggggt tcggcttctg    2640
gcgtgtgacc ggcggctcta gacaattgta ctaaccttct tctctttcct ctcctgacag    2700
gttggtgtac actagcggcc gccaccatgc cagcctcttt ctccgacgc atcctgattc    2760
gcaacaattc cgaccaagac gaactggata ccgaggccga gtctcgcgg agattggaga    2820
acaggcttgt gctgctgttc tttggcgcgg gagcgtgtcc tcagtgccag gctttcgtgc    2880
caatcctgaa ggatttcttc gtgcggctga ctgacgaatt ctacgtcctc cgggccgcc    2940
agctggcact ggtgtacgtg tcccaagact caaccgagga acagcaggat ctgttcctca    3000
aggacatgcc caaaaagtgg ctgttcctgc gtttgaggaa cgacttgcgg cgctagtgat    3060
cagcctcgac tgtgccttct agttgccagc catctgttgt ttgcccctcc cccgtgcctt    3120
```

```
ccttgaccct ggaaggtgcc actcccactg tcctttccta ataaaatgag gaaattgcat    3180
cgcattgtct gagtaggtgt cattctattc tgggggtgg ggtggggcag acagcaagg     3240
gggaggattg ggaagacaat agcaggcatg ctggggagga tccaatttat tctaaatgca    3300
taataaatac tgataacatc ttatagtttg tattatattt tgtattatcg ttgacatgta    3360
taattttgat atcaaaaact gattttccct ttattatttt cgagatttat tttcttaatt    3420
ctctttaaca aactagaaat attgtatata caaaaaatca taataatag atgaatagtt     3480
taattatagg tgttcatcaa tcgaaaaagc aacgtatctt atttaaagtg cgttgctttt    3540
ttctcattta aaggttaaa taattctcat atatcaagca aagtgacagg cgcccttaaa     3600
tattctgaca aatgctcttt ccctaaactc ccccataaa aaacccgcc gaagcgggtt      3660
tttacgttat ttgcggatta acgattactc gttatcagaa ccgcccagga agctttagtt    3720
attaatagta atcaattacg gggtcattag ttcatagccc atatatggag ttccgcgtta    3780
cataacttac ggtaaatggc ccgcctggct gaccgcccaa cgaccccgc ccattgacgt     3840
caataatgac gtatgttccc atagtaacgc aataggac tttccattga cgtcaatggg     3900
tggagtattt acggtaaact gcccacttgg cagtacatca agtgtatcat atgccaagta    3960
cgccccctat tgacgtcaat gacggtaaat ggcccgcctg gcattatgcc cagtacatga    4020
ccttatggga ctttcctact tggcagtaca tctacgtatt agtcatcgct attaacatgg    4080
tcgaggtgag ccccacgttc tgcttcactc tccccatctc cccccctcc caccccaa       4140
ttttgtattt atttattttt taattatttt gtgcagcgat ggggcgggg ggggggggg      4200
ggcgcgcgcc aggcggggcg gggcggggcg agggcgggg cggggcgagg cggagaggtg     4260
cggcggcagc caatcagagc ggcgcgctcc gaaagtttcc ttttatggcg aggcggcggc    4320
ggcggcggcc ctataaaaag cgaagcgcgc ggcgggcggg gagtcgctgc gacgctgcct    4380
tcgccccgtg ccccgctccg ccgccgcctc gcgccgcccg ccccggctct gactgaccgc    4440
gttactccca caggtgagcg gcgggatga gcacggcccg gcttcgggtg cggggctccg     4500
tacggggcgt ggcgcggggc tcgccgtgcc gggcgggggg tggcggcagg tgggggtgcc    4560
gggcggggcg gggccgcctc gggccgggga gggctcgggg gaggggcgcg gcggcccccg    4620
gagcgccggc ggctgtcgag gcgcggcgag ccgcagccat tgccttttat ggtaatcgtg    4680
cgagagggcg cagggacttc ctttgtccca aatctgtgcg gagccgaaat ctgggaggcg    4740
ccgccgcacc ccctctagcg ggcgcggggc gaagcggtgc ggcgccggca ggaaggaaat    4800
gggcggggag ggccttcgtg cgtcgccgcg ccgccgtccc cttctccctc tccagcctcg    4860
gggctgtccg cgggggacg gctgccttcg gggggacgg ggcagggcgg ggttcggctt      4920
ctggcgtgtg accggcggct ctagacaatt gtactaacct tcttctctt cctctcctga    4980
caggttggtg tacactaggc catacaggcc gccaccatgg cctcactgtt ctccgggcgc    5040
atcctcatcc gaaacaacag cgatcaggac gaattggaca ccgaggctga agtctcccgc    5100
cggctggaaa acaggctcgt gctcctgttc ttcggtgccg gagcgtgccc gcagtgccaa    5160
gccttcgtcc caattcttaa ggacttcttt gtgcgcctca ctgatgagtt ttacgtgctc    5220
cgggcagcgc agctggcctt ggtgtatgtg tcgcaagatt ccactgagga acaacaggac    5280
ctgttcctga aagacatgcc taagaagtgg cttttcctgc ccttcgagga cgacctgaga    5340
agggacctgg gacgccagtt cagcgtggaa cggctgccgg ccgtcgtggt gctgaagccc    5400
gacgggacg tgcttacccg ggatggcgct gacgaaatcc agaggctggg caccgcctgt    5460
ttcgcaaatt ggcaggaggc cgccgaagtg ctcgaccgga acttccagct gcccgaggat    5520
```

```
ctggaggacc aggaacctcg gtccctgacc gagtgcctca gacgccacaa gtaccgcgtg    5580
gaaaaggccg cgagaggagg acgggacccg ggtggcgggg gaggcgaaga gggcggagcc    5640
ggtggcctgt tctgatagat ctgcctcgac tgtgccttct agttgccagc catctgttgt    5700
ttgcccctcc cccgtgcctt ccttgaccct ggaaggtgcc actcccactg tcctttccta    5760
ataaaatgag gaaattgcat cgcattgtct gagtaggtgt cattctattc tggggggtgg    5820
ggtggggcag gacagcaagg gggaggattg ggaagacaat agcaggcatg ctggggactc    5880
gagttctacg tagataagta gcatggcggg ttaatcatta actacaagga acccctagtg    5940
atggagttgg ccactccctc tctgcgcgct cgctcgctca ctgaggccgg gcgaccaaag    6000
gtcgcccgac gcccgggctt tgcccgggcg gcctcagtga gcgagcgagc gcgcagcctt    6060
aattaaccta aggaaaatga agtgaagttc ctatactttc tagagaatag gaacttctat    6120
agtgagtcga ataagggcga cacaaaattt attctaaatg cataataaat actgataaca    6180
tcttatagtt tgtattatat tttgtattat cgttgacatg tataattttg atatcaaaaa    6240
ctgattttcc ctttattatt ttcgagattt attttcttaa ttctctttaa caaactagaa    6300
atattgtata tacaaaaaat cataataata agatgaatag tttaattata ggtgttcatc    6360
aatcgaaaaa gcaacgtatc ttatttaaag tgcgttgctt ttttctcatt tataaggtta    6420 ataattctc atatatcaag caaagtgaca ggcgccctta atattctga caaatgctct    6480 ttccctaaac tccccccata aaaaaacccg ccgaagcggg ttttacgtt atttgcggat    6540 taacgattac tcgttatcag aaccgcccag ggggcccgag cttaaccttt ttatttgggg    6600
gagagggaag tcatgaaaaa actaaccttt gaaattcgat ctccagcaca tcagcaaaac    6660
gctattcacg cagtcagca aatccttcca gacccaacca aaccaatcgt agtaaccatt    6720
caggaacgca accgcagctt agaccaaaac aggaagctat gggcctgctt aggtgacgtc    6780
tctcgtcagg ttgaatggca tggtcgctgg ctggatgcag aaagctggaa gtgtgtgttt    6840
accgcagcat taaagcagca ggatgttgtt cctaaccttg ccgggaatgg ctttgtggta    6900
ataggccagt caaccagcag gatgcgtgta ggcgaatttg cggagctatt agagcttata    6960
caggcattcg gtacagagcg tggcgttaag tggtcagacg aagcgagact ggctctggag    7020
tggaaagcga gatggggaga cagggctgca tgataaatgt cgttagtttc tccggtggca    7080
ggacgtcagc atatttgctc tggctaatgg agcaaaagcg acgggcaggt aaagacgtgc    7140
attacgtttt catggataca ggttgtgaac atccaatgac atatcggttt gtcagggaag    7200
ttgtgaagtt ctgggatata ccgctcaccg tattgcaggt tgatatcaac ccggagcttg    7260
gacagccaaa tggttatacg gtatgggaac caaaggatat tcagacgcga atgcctgttc    7320
tgaagccatt tatcgatatg gtaaagaaat atggcactcc atacgtcggc ggcgcgttct    7380
gcactgacag attaaaactc gttcccttca ccaaatactg tgatgaccat ttcgggcgag    7440
ggaattacac cacgtggatt ggcatcagag ctgatgaacc gaagcggcta aagccaaagc    7500
ctggaatcag atatcttgct gaactgtcag actttgagaa ggaagatatc ctcgcatggt    7560
ggaagcaaca accattcgat ttgcaaatac cggaacatct cggtaactgc atattctgca    7620
ttaaaaaatc aacgcaaaaa atcggacttg cctgcaaaga tgaggaggga ttgcagcgtg    7680 ttttaatga ggtcatcacg ggatcccatg tgcgtgacgg acatcgggaa acgccaaagg    7740
agattatgta ccgaggaaga atgtcgctgg acggtatcgc gaaaatgtat tcagaaaatg    7800
attatcaagc cctgtatcag gacatggtac gagctaaaag attcgatacc ggctcttgtt    7860
```

```
ctgagtcatg cgaaatattt ggagggcagc ttgatttcga cttcgggagg gaagctgcat    7920
gatgcgatgt tatcggtgcg gtgaatgcaa agaagataac cgcttccgac caaatcaacc    7980
ttactggaat cgatggtgtc tccggtgtga agaacacca  acagggtgt  taccactacc    8040 gcaggaaaag gaggacgtgt ggcgagacag cgacgaagta tcaccgacat aatctgcgaa    8100
aactgcaaat accttccaac gaaacgcacc agaaataaac ccaagccaat cccaaaagaa    8160
tctgacgtaa aaaccttcaa ctacacggct cacctgtggg atatccggtg gctaagacgt    8220
cgtgcgagga aaacaaggtg attgaccaaa atcgaagtta cgaacaagaa agcgtcgagc    8280
gagctttaac gtgcgctaac tgcggtcaga agctgcatgt gctggaagtt cacgtgtgtg    8340
agcactgctg cgcagaactg atgagcgatc cgaatagctc gatgcacgag gaagaagatg    8400
atggctaaac cagcgcgaag acgatgtaaa acgatgaat  gccgggaatg gtttcaccct    8460
gcattcgcta atcagtggtg gtgctctcca gagtgtggaa ccaagatagc actcgaacga    8520
cgaagtaaag aacgcgaaaa agcggaaaaa gcagcagaga agaaacgacg acgagaggag    8580
cagaaacaga aagataaact taagattcga aaactcgcct taaagccccg cagttactgg    8640
attaaacaag cccaacaagc cgtaaacgcc ttcatcagag aaagagaccg cgacttacca    8700
tgtatctcgt gcggaacgct cacgtctgct cagtgggatg ccggacatta ccggacaact    8760
gctgcggcac ctcaactccg atttaatgaa cgcaatattc acaagcaatg cgtggtgtgc    8820
aaccagcaca aaagcggaaa tctcgttccg tatcgcgtcg aactgattag ccgcatcggg    8880
caggaagcag tagacgaaat cgaatcaaac cataaccgcc atcgctggac tatcgaagag    8940
tgcaaggcga tcaaggcaga gtaccaacag aaactcaaag acctgcgaaa tagcagaagt    9000
gaggccgcat gacgttctca gtaaaaacca ttccagacat gctcgttgaa gcatacggaa    9060
atcagacaga agtagcacgc agactgaaat gtagtcgcgg tacggtcaga aaatacgttg    9120
atgataaaga cgggaaaatg cacgccatcg tcaacgacgt tctcatggtt catcgcggat    9180
ggagtgaaag agatgcgcta ttacgaaaaa attgatggca gcaaataccg aaatatttgg    9240
gtagttggcg atctgcacgg atgctacacg aacctgatga acaaactgga tacgattgga    9300
ttcgacaaca aaaagacct  gcttatctcg gtgggcgatt tggttgatcg tggtgcagag    9360
aacgttgaat gcctggaatt aatcacattc ccctggttca gagctgtacg tggaaaccat    9420
gagcaaatga tgattgatgg cttatcagag cgtggaaacg ttaatcactg gctgcttaat    9480
ggcggtggct ggttctttaa tctcgattac gacaaagaaa ttctggctaa agctcttgcc    9540
cataaagcag atgaacttcc gttaatcatc gaactggtga gcaaagataa aaaatatgtt    9600
atctgccacg ccgattatcc ctttgacgaa tacgagtttg gaaagccagt tgatcatcag    9660
caggtaatct ggaaccgcga acgaatcagc aactcacaaa acgggatcgt gaaagaaatc    9720
aaaggcgcgg acacgttcat ctttggtcat acgccagcag tgaaaccact caagtttgcc    9780
aaccaaatgt atatcgatac cggcgcagtg ttctgcggaa acctaacatt gattcaggta    9840
cagggagaag gcgcatgaga ctcgaaagcg tagctaaatt tcattcgcca aaaagcccga    9900
tgatgagcga ctcaccacgg gccacggctt ctgactctct ttccggtact gatgtgatgg    9960
ctgctatggg gatggcgcaa tcacaagccg gattcggtat ggctgcattc tgcggtaagc   10020
acgaactcag ccagaacgac aaacaaaagg ctatcaacta tctgatgcaa tttgcacaca   10080
aggtatcggg gaaataccgt ggtgtggcaa agcttgaagg aaatactaag gcaaaggtac   10140
tgcaagtgct cgcaacattc gcttatgcgg attattgccg tagtgccgcg acgccggggg   10200
caagatgcag agattgccat ggtacaggcc gtgcggttga tattgccaaa acagagctgt   10260
```

```
gggggagagt tgtcgagaaa gagtgcggaa gatgcaaagg cgtcggctat tcaaggatgc   10320
cagcaagcgc agcatatcgc gctgtgacga tgctaatccc aaaccttacc caacccacct   10380
ggtcacgcac tgttaagccg ctgtatgacg ctctggtggt gcaatgccac aaagaagagt   10440
caatcgcaga caacatttg aatgcggtca cacgttagca gcatgattgc cacggatggc   10500
aacatattaa cggcatgata ttgacttatt gaataaaatt gggtaaattt gactcaacga   10560
tgggttaatt cgctcgttgt ggtagtgaga tgaaagagg cggcgcttac taccgattcc   10620
gcctagttgg tcacttcgac gtatcgtctg gaactccaac catcgcaggc agagaggtct   10680
gcaaaatgca atcccgaaac agttcgcagg taatagttag agcctgcata acggtttcgg   10740
gattttttat atctgcacaa caggtaagag cattgagtcg ataatcgtga agagtcggcg   10800
agcctggtta gccagtgctc tttccgttgt gctgaattaa gcgaataccg gaagcagaac   10860
cggatcacca aatgcgtaca ggcgtcatcg ccgcccagca acagcacaac ccaaactgag   10920
ccgtagccac tgtctgtcct gaattcatta gtaatagtta cgctgcggcc ttttacacat   10980
gaccttcgtg aaagcgggtg gcaggaggtc gcgctaacaa cctcctgccg ttttgcccgt   11040
gcatatcggt cacgaacaaa tctgattact aaacacagta gcctggattt gttctatcag   11100
taatcgacct tattcctaat taaatagagc aaatcccctt attggggta agacatgaag   11160 atgccagaaa aacatgacct gttggccgcc attctcgcgg caaggaaca aggcatcggg   11220 gcaatccttg cgtttgcaat ggcgtacctt cgcggcagat ataatggcgg tgcgtttaca   11280
aaaacagtaa tcgacgcaac gatgtgcgcc attatcgcct ggttcattcg tgaccttctc   11340
gacttcgccg gactaagtag caatctcgct tatataacga gcgtgtttat cggctacatc   11400
ggtactgact cgattggttc gcttatcaaa cgcttgctg ctaaaaaagc cggagtagaa   11460
gatggtagaa atcaataatc aacgtaaggc gttcctcgat atgctggcgt ggtcggaggg   11520
aactgataac ggacgtcaga aaccagaaa tcatggttat gacgtcattg taggcggaga   11580
gctatttact gattactccg atcaccctcg caaacttgtc acgctaaacc caaaactcaa   11640
atcaacaggc gcttaagact ggccgtcgtt ttacaacaca gaaagagttt gtagaaacgc   11700
aaaaaggcca tccgtcaggg gccttctgct tagtttgatg cctggcagtt ccctactctc   11760
gccttccgct tcctcgctca ctgactcgct gcgctcggtc gttcggctgc ggcgagcggt   11820
atcagctcac tcaaaggcgg taatacggtt atccacagaa tcaggggata acgcaggaaa   11880
gaacatgtga gcaaaaggcc agcaaaaggc caggaaccgt aaaaaggccg cgttgctggc   11940
gtttttccat aggctccgcc ccctgacga gcatcacaaa aatcgacgct caagtcagag   12000
gtggcgaaac ccgacaggac tataaagata ccaggcgttt ccccctggaa gctccctcgt   12060
gcgctctcct gttccgaccc tgccgcttac cggatacctg tccgcctttc tcccttcggg   12120
aagcgtggcg ctttctcata gctcacgctg taggtatctc agttcggtgt aggtcgttcg   12180
ctccaagctg ggctgtgtgc acgaaccccc cgttcagccc gaccgctgcg ccttatccgg   12240
taactatcgt cttgagtcca acccggtaag acacgactta tcgccactgg cagcagccac   12300
tggtaacagg attagcagag cgaggtatgt aggcggtgct acagagttct tgaagtggtg   12360
ggctaactac ggctacacta agaacagt atttggtatc tgcgctctgc tgaagccagt   12420
taccttcgga aaagagttg gtagctcttg atccggcaaa caaaccaccg ctggtagcgg   12480
tggttttttt gtttgcaagc agcagattac gcgcagaaaa aaaggatctc aagaagatcc   12540
tttgatcttt tctacggggt ctgacgctca gtggaacgac gcgcgcgtaa ctcacgttaa   12600
```

```
gggatttttgg tcatgagctt gcgccgtccc gtcaagtcag cgtaatgctc tgcttt       12656
```

<210> SEQ ID NO 8
<211> LENGTH: 4727
<212> TYPE: DNA
<213> ORGANISM: Artificial Sequence
<220> FEATURE:
<223> OTHER INFORMATION: rAAV genome  expressing two copies of human
      RdCVF codon optimized short form sequences
<220> FEATURE:
<221> NAME/KEY: misc_feature
<222> LOCATION: (9)..(100)
<223> OTHER INFORMATION: KanR complement
<220> FEATURE:
<221> NAME/KEY: misc_feature
<222> LOCATION: (117)..(246)
<223> OTHER INFORMATION: AAV 5'  ITR
<220> FEATURE:
<221> NAME/KEY: promoter
<222> LOCATION: (307)..(1578)
<220> FEATURE:
<221> NAME/KEY: gene
<222> LOCATION: (1579)..(1926)
<223> OTHER INFORMATION: human optimized RdCVF short form
<220> FEATURE:
<221> NAME/KEY: polyA_signal
<222> LOCATION: (1931)..(2152)
<220> FEATURE:
<221> NAME/KEY: terminator
<222> LOCATION: (2237)..(2537)
<220> FEATURE:
<221> NAME/KEY: misc_feature
<222> LOCATION: (2328)..(2353)
<223> OTHER INFORMATION: pTF3 complement
<220> FEATURE:
<221> NAME/KEY: terminator
<222> LOCATION: (2544)..(2657)
<220> FEATURE:
<221> NAME/KEY: promoter
<222> LOCATION: (2688)..(3959)
<220> FEATURE:
<221> NAME/KEY: gene
<222> LOCATION: (3960)..(4307)
<223> OTHER INFORMATION: human optimized RdCVF short form second copy
<220> FEATURE:
<221> NAME/KEY: polyA_signal
<222> LOCATION: (4312)..(4533)
<220> FEATURE:
<221> NAME/KEY: misc_feature
<222> LOCATION: (4581)..(4710)
<223> OTHER INFORMATION: AAV 3' ITR

<400> SEQUENCE: 8

```
tagaaaaact catcgagcat caaatgaaac tgcaatttat tcatatcagg attatcaata     60 ccatatttt gaaaaagccg tttctgtaat gaaggagaaa gtcgacttaa ttaaggctgc     120
gcgctcgctc gctcactgag gccgcccggg caaagcccgg gcgtcgggcg acctttggtc    180
gcccggcctc agtgagcgag cgagcgcgca gagagggagt ggccaactcc atcactaggg    240
gttccttgta gttaatgatt aacccgccat gctacttatc tacgtagcaa gctagctagt    300
tattaatagt aatcaattac ggggtcatta gttcatagcc catatatgga gttccgcgtt    360
acataactta cggtaaatgg cccgcctggc tgaccgccca acgacccccg cccattgacg    420
tcaataatga cgtatgttcc catagtaacg ccaatagggga ctttccattg acgtcaatgg    480
gtggagtatt tacggtaaac tgcccacttg gcagtacatc aagtgtatca tatgccaagt    540 acgccccta ttgacgtcaa tgacggtaaa tggcccgcct ggcattatgc ccagtacatg    600 acctatggg actttcctac ttggcagtac atctacgtat tagtcatcgc tattaacatg    660
gtcgaggtga gccccacgtt ctgcttcact ctccccatct ccccccctc cccacccca    720
```

```
attttgtatt tatttattttt ttaattattt tgtgcagcga tgggggcggg ggggggggggg    780 gggcgcgcgc caggcggggc ggggcggggc gaggggcggg gcggggcgag gcggagaggt    840
gcggcggcag ccaatcagag cggcgcgctc cgaaagtttc cttttatggc gaggcggcgg    900
cggcggcggc cctataaaaa gcgaagcgcg cggcggggcgg ggagtcgctg cgacgctgcc    960
ttcgccccgt gccccgctcc gccgccgcct cgcgccgccc gccccggctc tgactgaccg   1020
cgttactccc acaggtgagc gggcgggatg agcacggccc ggcttcgggt gcgggctcc    1080 gtacggggcg tggcgcgggg ctcgccgtgc cgggcggggg gtggcggcag gtggggtgc    1140 cgggcggggc ggggccgcct cgggccgggg agggctcggg ggaggggcgc ggcggccccc   1200
ggagcgccgg cggctgtcga ggcgcggcga gccgcagcca ttgcctttta tggtaatcgt   1260
gcgagagggc gcagggactt cctttgtccc aaatctgtgc ggagccgaaa tctgggaggc   1320
gccgccgcac cccctctagc gggcgcgggg cgaagcggtg cggcgccggc aggaaggaaa   1380
tgggcgggga gggccttcgt gcgtcgccgc gccgccgtcc ccttctccct ctccagcctc   1440
ggggctgtcc gcggggggac ggctgccttc ggggggacg gggcagggcg gggttcggct    1500
tctggcgtgt gaccggcggc tctagacaat tgtactaacc ttcttctctt tcctctcctg   1560
acaggttggt gtacactagc ggccgccacc atggccagcc tcttctccgg acgcatcctg   1620
attcgcaaca attccgacca agacgaactg gataccgagg ccgaagtctc gcggagattg   1680
gagaacaggc ttgtgctgct gttctttggc gcggagcgt gtcctcagtg ccaggctttc    1740
gtgccaatcc tgaaggattt cttcgtgcgg ctgactgacg aattctacgt cctccgggcc   1800
gcccagctgg cactggtgta cgtgtcccaa gactcaaccg aggaacagca ggatctgttc   1860
ctcaaggaca tgcccaaaaa gtggctgttc ctgccgtttg aggacgactt gcggcgctag   1920
tgatcaaaga gatctgcctc gactgtgcct tctagttgcc agccatctgt tgtttgcccc   1980
tcccccgtgc cttccttgac cctggaaggt gccactccca ctgtcctttc ctaataaaat   2040
gaggaaattg catcgcattg tctgagtagg tgtcattcta ttctgggggg tggggtgggg   2100
caggacagca agggggagga ttgggaagac aatagcaggc atgctgggga ctcgataagg   2160
aaaatgaagt gaagttccta tactttctag agaataggaa cttctatagt gagtcgaata   2220
agggcgacac aaaatttatt ctaaatgcat aataaatact gataacatct tatagtttgt   2280
attatatttt gtattatcgt tgacatgtat aattttgata tcaaaaactg atttttccctt   2340 tattattttc gagatttatt ttcttaattc tctttaacaa actagaaata ttgtatatac   2400
aaaaaatcat aaataataga tgaatagttt aattataggt gttcatcaat cgaaaaagca   2460
acgtatctta tttaaagtgc gttgcttttt tctcatttat aaggttaaat aattctcata   2520
tatcaagcaa agtgacaggc gcccttaaat attctgacaa atgctctttc cctaaactcc   2580
ccccataaaa aaacccgccg aagcgggttt ttacgttatt tgcggattaa cgattactcg   2640
ttatcagaac cgcccagggg gcccgagctt aactagctag ttattaatag taatcaatta   2700
cggggtcatt agttcatagc ccatatatgg agttccgcgt tacataactt acggtaaatg   2760
gcccgcctgg ctgaccgccc aacgaccccc gcccattgac gtcaataatg acgtatgttc   2820
ccatagtaac gccaataggg actttccatt gacgtcaatg ggtggagtat ttacggtaaa   2880
ctgcccactt ggcagtacat caagtgtatc atatgccaag tacgccccct attgacgtca   2940
atgacggtaa atggcccgcc tggcattatg cccagtacat gaccttatgg gactttccta   3000
cttggcagta catctacgta ttagtcatcg ctattaacat ggtcgaggtg agccccacgt   3060
tctgcttcac tctccccatc tccccccccct ccccaccccc aattttgtat ttatttattt   3120
```

```
tttaattatt ttgtgcagcg atggggggcgg gggggggggg ggggcgcgcg ccaggcgggg    3180
cggggcgggg cgaggggcgg ggcggggcga ggcggagagg tgcggcggca gccaatcaga    3240
gcggcgcgct ccgaaagttt ccttttatgg cgaggcggcg gcggcggcgg ccctataaaa    3300
agcgaagcgc gcggcgggcg gggagtcgct gcgacgctgc cttcgcccg tgccccgctc     3360
cgccgccgcc tcgcgccgcc cgccccggct ctgactgacc gcgttactcc cacaggtgag    3420
cgggcgggat gagcacggcc cggcttcggg tgcggggctc cgtacggggc gtggcgcggg    3480
gctcgccgtg ccgggcgggg ggtggcggca ggtgggggtg ccgggcgggg cggggccgcc    3540
tcgggccggg gagggctcgg gggaggggcg cggcggcccc cggagcgccg gcggctgtcg    3600
aggcgcggcg agccgcagcc attgcctttt atggtaatcg tgcgagaggg cgcagggact    3660
tcctttgtcc caaatctgtg cggagccgaa atctgggagg cgccgccgca ccccctctag    3720
cgggcgcggg gcgaagcggt gcggcgccgg caggaaggaa atgggcgggg agggccttcg    3780
tgcgtcgccg cgccgccgtc cccttctccc tctccagcct cggggctgtc cgcgggggga    3840
cggctgcctt cgggggggac ggggcagggc ggggttcggc ttctggcgtg tgaccggcgg    3900
ctctagacaa ttgtactaac cttcttctct ttcctctcct gacaggttgg tgtacactag    3960
cggccgccac catggccagc ctcttctccg gacgcatcct gattcgcaac aattccgacc    4020
aagacgaact ggataccgag gccgaagtct cgcggagatt ggagaacagg cttgtgctgc    4080
tgttctttgg cgcgggagcg tgtcctcagt gccaggcttt cgtgccaatc ctgaaggatt    4140
tcttcgtgcg gctgactgac gaattctacg tcctccgggc cgcccagctg gcactggtgt    4200
acgtgtccca agactcaacc gaggaacagc aggatctgtt cctcaaggac atgcccaaaa    4260
agtggctgtt cctgccgttt gaggacgact tgccggcgcta gtgatcaaag agatctgcct    4320
cgactgtgcc ttctagttgc cagccatctg ttgtttgccc ctcccccgtg ccttccttga    4380
ccctggaagg tgccactccc actgtccttt cctaataaaa tgaggaaatt gcatcgcatt    4440
gtctgagtag gtgtcattct attctggggg gtggggtggg gcaggacagc aaggggagg     4500
attgggaaga caatagcagg catgctgggg actcgagttc tacgtagata agtagcatgg    4560
cgggttaatc attaactaca aggaaccccct agtgatgag ttggccactc cctctctgcg    4620
cgctcgctcg ctcactgagg ccgggcgacc aaaggtcgcc cgacgcccgg gctttgcccg    4680
ggcggcctca gtgagcgagc gagcgcgcag ccttaattaa cctaagg                  4727
```

<210> SEQ ID NO 9
<211> LENGTH: 12446
<212> TYPE: DNA
<213> ORGANISM: Artificial Sequence
<220> FEATURE:
<223> OTHER INFORMATION: plasmid expressing rAAV genome with two copies of optimized human RdCVF short form
<220> FEATURE:
<221> NAME/KEY: misc_feature
<222> LOCATION: (9)..(803)
<223> OTHER INFORMATION: KanR complement
<220> FEATURE:
<221> NAME/KEY: misc_feature
<222> LOCATION: (988)..(1162)
<223> OTHER INFORMATION: B1 B2 T1 Txn Terminator Complement
<220> FEATURE:
<221> NAME/KEY: misc_feature
<222> LOCATION: (1063)..(1079)
<223> OTHER INFORMATION: pTR
<220> FEATURE:
<221> NAME/KEY: misc_feature
<222> LOCATION: (1253)..(1382)
<223> OTHER INFORMATION: 5' AAV ITR

```
<220> FEATURE:
<221> NAME/KEY: promoter
<222> LOCATION: (1443)..(2714)
<220> FEATURE:
<221> NAME/KEY: gene
<222> LOCATION: (2715)..(3062)
<223> OTHER INFORMATION: human optimized RdCVF short form
<220> FEATURE:
<221> NAME/KEY: polyA_signal
<222> LOCATION: (3067)..(3288)
<220> FEATURE:
<221> NAME/KEY: terminator
<222> LOCATION: (3373)..(3673)
<220> FEATURE:
<221> NAME/KEY: misc_feature
<222> LOCATION: (3464)..(3489)
<223> OTHER INFORMATION: pTF3 complement
<220> FEATURE:
<221> NAME/KEY: terminator
<222> LOCATION: (3680)..(3793)
<220> FEATURE:
<221> NAME/KEY: promoter
<222> LOCATION: (3824)..(5095)
<220> FEATURE:
<221> NAME/KEY: gene
<222> LOCATION: (5096)..(5443)
<223> OTHER INFORMATION: human optimized RdCVF short form second copy
<220> FEATURE:
<221> NAME/KEY: polyA_signal
<222> LOCATION: (5448)..(5669)
<220> FEATURE:
<221> NAME/KEY: misc_feature
<222> LOCATION: (5717)..(5846)
<223> OTHER INFORMATION: AAV 3' ITR
<220> FEATURE:
<221> NAME/KEY: terminator
<222> LOCATION: (5940)..(6240)
<220> FEATURE:
<221> NAME/KEY: misc_feature
<222> LOCATION: (6031)..(6056)
<223> OTHER INFORMATION: pTF3 Complement
<220> FEATURE:
<221> NAME/KEY: terminator
<222> LOCATION: (6247)..(6360)
<220> FEATURE:
<221> NAME/KEY: misc_feature
<222> LOCATION: (6376)..(11442)
<223> OTHER INFORMATION: Lambda Stuffer
<220> FEATURE:
<221> NAME/KEY: misc_feature
<222> LOCATION: (11603)..(12406)
<223> OTHER INFORMATION: pUC Ori Complement

<400> SEQUENCE: 9
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa aataaggtta tcaagtgaga atcaccatg agtgacgact      240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
```

```
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttaggggtgt cgcccttat tcgactctat agtgaagttc    1200
ctattctcta gaaagtatag gaacttctga agtggggtcg acttaattaa ggctgcgcgc   1260
tcgctcgctc actgaggccg cccgggcaaa gcccggcgt cgggcgacct ttggtcgccc    1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga ccccgccca ttgacgtcaa     1560 taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc ccctcccca ccccaatttt    1860 tgtatttatt tattttttaa ttattttgtg cagcgatggg ggcgggggg ggggggggc     1920 gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggatgagca cggcccggct tcgggtgcgg ggctccgtac   2220
ggggcgtggc gcgggctcg ccgtgccggg cggggggtgg cggcaggtgg gggtgccggg   2280
cggggcgggg ccgcctcggg ccggggaggg ctcggggag gggcgcggcg gccccggag    2340 cgccggcggc tgtcgaggcg cggcgagccg cagccattgc cttttatggt aatcgtgcga   2400
gagggcgcag ggacttcctt tgtcccaaat ctgtgcggag ccgaaatctg ggaggcgccg   2460
ccgcaccccc tctagcgggc gcggggcgaa gcggtgcggc gccggcagga aggaaatggg   2520
cggggagggc cttcgtgcgt cgccgcgccg ccgtccccctt ctccctctcc agcctcgggg   2580
ctgtccgcgg gggacggct gccttcgggg gggacggggc agggcggggt tcggcttctg   2640
gcgtgtgacc ggcggctcta gacaattgta ctaaccttct tctctttcct tcctgacag    2700 gttggtgtac actagcggcc gccaccatgg ccagcctctt ctccggacgc atcctgattc   2760
gcaacaattc cgaccaagac gaactggata ccgaggccga gtctcgcggg agattggaga   2820
acaggcttgt gctgctgttc tttgcgcgcg gagcgtgtcc tcagtgccag gctttcgtgc   2880
caatcctgaa ggatttcttc gtgcggctga ctgacgaatt ctacgtcctc cgggccgccc   2940
agctggcact ggtgtacgtg tcccaagact caaccgagga acagcaggat ctgttcctca   3000
aggacatgcc caaaaagtgg ctgttcctgc cgtttgagga cgacttgcgg cgctagtgat   3060
caaagagatc tgcctcgact gtgccttcta gttgccagcc atctgttgtt tgcccctccc   3120
```

```
ccgtgccttc cttgaccctg gaaggtgcca ctcccactgt cctttcctaa taaaatgagg    3180
aaattgcatc gcattgtctg agtaggtgtc attctattct gggggggtggg gtggggcagg    3240 acagcaaggg ggaggattgg gaagacaata gcaggcatgc tggggactcg ataaggaaaa    3300
tgaagtgaag ttcctatact ttctagagaa taggaacttc tatagtgagt cgaataaggg    3360
cgacacaaaa tttattctaa atgcataata aatactgata acatcttata gtttgtatta    3420
tattttgtat tatcgttgac atgtataatt ttgatatcaa aaactgattt tcccttatt    3480 attttcgaga tttattttct taattctctt taacaaacta gaaatattgt atatacaaaa    3540
aatcataaat aatagatgaa tagtttaatt ataggtgttc atcaatcgaa aaagcaacgt    3600
atcttattta aagtgcgttg ctttttttctc atttataagg ttaaataatt ctcatatatc    3660
aagcaaagtg acaggcgccc ttaaatattc tgacaaatgc tctttcccta aactcccccc    3720
ataaaaaaac cgccgaagc gggttttac gttatttgcg gattaacgat tactcgttat    3780
cagaaccgcc caggggcccc gagcttaact agctagttat taatagtaat caattacggg    3840
gtcattagtt catagcccat atatggagtt ccgcgttaca taacttacgg taaatggccc    3900
gcctggctga ccgcccaacg accccgccc attgacgtca ataatgacgt atgttcccat    3960
agtaacgcca atagggactt tccattgacg tcaatgggtg gagtatttac ggtaaactgc    4020
ccacttggca gtacatcaag tgtatcatat gccaagtacg ccccctattg acgtcaatga    4080
cggtaaatgg cccgcctggc attatgccca gtacatgacc ttatgggact ttcctacttg    4140
gcagtacatc tacgtattag tcatcgctat taacatggtc gaggtgagcc ccacgttctg    4200
cttcactctc cccatctccc ccccctcccc accccccaatt ttgtatttat ttatttttta    4260 attatttgt gcagcgatgg gggcggggg gggggggggg cgcgcgccag gcggggcggg    4320
gcggggcgag gggcggggcg gggcgaggcg gagaggtgcg gcggcagcca atcagagcgg    4380
cgcgctccga aagtttcctt ttatggcgag gcggcggcgg cggcggccct ataaaaagcg    4440
aagcgcgcgg cgggcgggga gtcgctgcga cgctgccttc gccccgtgcc ccgctccgcc    4500
gccgcctcgc gccgcccgcc ccggctctga ctgaccgcgt tactcccaca ggtgagcggg    4560
cgggatgagc acggcccggc ttcgggtgcg ggctccgta cggggcgtgg cgcggggctc    4620
gccgtgccgg gcggggggtg gcggcaggtg ggggtgccgg gcggggcggg gccgcctcgg    4680
gccggggagg gctcggggga gggcgcggc ggccccgga gcgccggcgg ctgtcgaggc    4740
gcggcgagcc gcagccattg ccttttatgg taatcgtgcg agagggcgca gggacttcct    4800
ttgtcccaaa tctgtgcgga gccgaaatct gggaggcgcc gccgcacccc ctctagcggg    4860
cgcggggcga agcggtgcgg cgccggcagg aaggaaatgg gcgggagggc cttcgtgcg    4920 tcgccgcgcc gccgtcccct tctccctctc cagcctcggg gctgtccgcg ggggacggc    4980 tgccttcggg ggacgggg cagggcgggg ttcggcttct ggcgtgtgac cggcggctct    5040
agacaattgt actaaccttc ttctctttcc tctcctgaca ggttggtgta cactagcggc    5100
cgccaccatg gccagcctct tctccggacg catcctgatt cgcaacaatt ccgaccaaga    5160
cgaactggat accgaggccg aagtctcgcg gagattggag aacaggcttg tgctgctgtt    5220
ctttggcgcg ggagcgtgtc ctcagtgcca ggctttcgtg ccaatcctga aggatttctt    5280
cgtgcggctg actgacgaat tctacgtcct ccgggccgcc cagctggcac tggtgtacgt    5340
gtcccaagac tcaaccgagg aacagcagga tctgttcctc aaggacatgc ccaaaaagtg    5400
gctgttcctg ccgtttgagg acgacttgcg gcgctagtga tcaaagagat ctgcctcgac    5460
```

```
tgtgccttct agttgccagc catctgttgt ttgcccctcc cccgtgcctt ccttgaccct    5520
ggaaggtgcc actcccactg tcctttccta ataaaatgag gaaattgcat cgcattgtct    5580
gagtaggtgt cattctattc tggggggtgg ggtggggcag gacagcaagg gggaggattg    5640
ggaagacaat agcaggcatg ctggggactc gagttctacg tagataagta gcatggcggg    5700
ttaatcatta actacaagga accectagtg atggagttgg ccactccctc tctgcgcgct    5760
cgctcgctca ctgaggccgg gcgaccaaag gtcgcccgac gcccgggctt gcccggggcg    5820
gcctcagtga gcgagcgagc gcgcagcctt aattaaccta aggaaaatga agtgaagttc    5880
ctatactttc tagagaatag gaacttctat agtgagtcga taagggcga cacaaaattt    5940 attctaaatg cataataaat actgataaca tcttatagtt tgtattatat tttgtattat    6000
cgttgacatg tataattttg atatcaaaaa ctgattttcc ctttattatt ttcgagattt    6060
attttcttaa ttctctttaa caaactagaa atattgtata tacaaaaaat cataaataat    6120
agatgaatag tttaattata ggtgttcatc aatcgaaaaa gcaacgtatc ttatttaaag    6180
tgcgttgctt ttttctcatt tataaggtta aataattctc atatatcaag caaagtgaca    6240
ggcgccctta aatattctga caaatgctct ttccctaaac tccccccata aaaaaacccg    6300
ccgaagcggg ttttttacgtt atttgcggat taacgattac tcgttatcag aaccgcccag    6360
ggggcccgag cttaaccttt ttatttgggg gagagggaag tcatgaaaaa actaaccttt    6420
gaaattcgat ctccagcaca tcagcaaaac gctattcacg cagtacagca aatccttcca    6480
gacccaacca aaccaatcgt agtaaccatt caggaacgca accgcagctt agaccaaaac    6540
aggaagctat gggcctgctt aggtgacgtc tctcgtcagg ttgaatggca tggtcgctgg    6600
ctggatgcag aaagctggaa gtgtgtgttt accgcagcat taaagcagca ggatgttgtt    6660
cctaaccttg ccgggaatgg ctttgtggta ataggccagt caaccagcag gatgcgtgta    6720
ggcgaatttg cggagctatt agagcttata caggcattcg gtacagagcg tggcgttaag    6780
tggtcagacg aagcgagact ggctctggag tggaaagcga gatggggaga cagggctgca    6840
tgataaatgt cgttagtttc tccggtggca ggacgtcagc atatttgctc tggctaatgg    6900
agcaaaagcg acgggcaggt aaagacgtgc attacgtttt catggataca ggttgtgaac    6960
atccaatgac atatcggttt gtcagggaag ttgtgaagtt ctgggatata ccgctcaccg    7020
tattgcaggt tgatatcaac ccggagcttg acagccaaa tggttatacg gtatgggaac    7080
caaaggatat tcagacgcga atgcctgttc tgaagccatt tatcgatatg gtaaagaaat    7140
atggcactcc atacgtcggc ggcgcgttct gcactgacag attaaaactc gttcccttca    7200
ccaaatactg tgatgaccat ttcgggcgag ggaattacac cacgtggatt ggcatcagag    7260
ctgatgaacc gaagcggcta aagccaaagc ctggaatcag atatcttgct gaactgtcag    7320
actttgagaa ggaagatatc ctcgcatggt ggaagcaaca accattcgat ttgcaaatac    7380
cggaacatct cggtaactgc atattctgca ttaaaaaatc aacgcaaaaa atcggacttg    7440
cctgcaaaga tgaggaggga ttgcagcgtg ttttaatga ggtcatcacg ggatcccatg    7500
tgcgtgacgg acatcgggaa acgccaaagg agattatgta ccgaggaaga atgtcgctgg    7560
acggtatcgc gaaaatgtat tcagaaaatg attatcaagc cctgtatcag gacatggtac    7620
gagctaaaag attcgatacc ggctcttgtt ctgagtcatg cgaaatattt ggagggcagc    7680
ttgatttcga cttcgggagg gaagctgcat gatgcgatgt tatcggtgcg gtgaatgcaa    7740
agaagataac cgcttccgac caaatcaacc ttactggaat cgatggtgtc tccggtgtga    7800
aagaacacca acagggtgt taccactacc gcaggaaaag gaggacgtgt ggcgagacag    7860
```

```
cgacgaagta tcaccgacat aatctgcgaa aactgcaaat accttccaac gaaacgcacc    7920
agaaataaac ccaagccaat cccaaaagaa tctgacgtaa aaaccttcaa ctacacggct    7980
cacctgtggg atatccggtg gctaagacgt cgtgcgagga aaacaaggtg attgaccaaa    8040
atcgaagtta cgaacaagaa agcgtcgagc gagctttaac gtgcgctaac tgcggtcaga    8100
agctgcatgt gctggaagtt cacgtgtgtg agcactgctg cgcagaactg atgagcgatc    8160
cgaatagctc gatgcacgag gaagaagatg atggctaaac cagcgcgaag acgatgtaaa    8220
aacgatgaat gccgggaatg gtttcaccct gcattcgcta atcagtggtg gtgctctcca    8280
gagtgtggaa ccaagatagc actcgaacga cgaagtaaag aacgcgaaaa agcggaaaaa    8340
gcagcagaga agaaacgacg acgagaggag cagaaacaga agataaaact taagattcga    8400
aaactcgcct taaagcccg cagttactgg attaaacaag cccaacaagc cgtaaacgcc    8460
ttcatcagag aaagagaccg cgacttacca tgtatctcgt gcggaacgct cacgtctgct    8520
cagtgggatg ccggacatta ccggacaact gctgcggcac ctcaactccg atttaatgaa    8580
cgcaatattc acaagcaatg cgtggtgtgc aaccagcaca aaagcggaaa tctcgttccg    8640
tatcgcgtcg aactgattag ccgcatcggg caggaagcag tagacgaaat cgaatcaaac    8700
cataaccgcc atcgctggac tatcgaagag tgcaaggcga tcaaggcaga gtaccaacag    8760
aaactcaaag acctgcgaaa tagcagaagt gaggccgcat gacgttctca gtaaaaacca    8820
ttccagacat gctcgttgaa gcatacggaa atcagacaga agtagcacgc agactgaaat    8880
gtagtcgcgg tacggtcaga aaatacgttg atgataaaga cgggaaaatg cacgccatcg    8940
tcaacgacgt tctcatggtt catcgcggat ggagtgaaag agatgcgcta ttacgaaaaa    9000
attgatggca gcaaataccg aaatatttgg gtagttggcg atctgcacgg atgctacacg    9060
aacctgatga acaaactgga tacgattgga ttcgacaaca aaaaagacct gcttatctcg    9120
gtgggcgatt tggttgatcg tggtgcagag aacgttgaat gcctggaatt aatcacattc    9180
ccctggttca gagctgtacg tggaaaccat gagcaaatga tgattgatgg cttatcagag    9240
cgtggaaacg ttaatcactg gctgcttaat ggcggtggct ggttctttaa tctcgattac    9300
gacaaagaaa ttctggctaa agctcttgcc cataaagcag atgaacttcc gttaatcatc    9360
gaactggtga gcaaagataa aaaatatgtt atctgccacg ccgattatcc ctttgacgaa    9420
tacgagtttg gaaagccagt tgatcatcag caggtaatct ggaaccgcga acgaatcagc    9480
aactcacaaa acgggatcgt gaaagaaatc aaaggcgcgg acacgttcat ctttggtcat    9540
acgccagcag tgaaaccact caagtttgcc aaccaaatgt atatcgatac cggcgcagtg    9600
ttctgcggaa acctaacatt gattcaggta cagggagaag gcgcatgaga ctcgaaagcg    9660
tagctaaatt tcattcgcca aaaagcccga tgatgagcga ctcaccacgg gccacggctt    9720
ctgactctct ttccggtact gatgtgatgg ctgctatggg gatggcgcaa tcacaagccg    9780
gattcggtat ggctgcattc tgcggtaagc acgaactcag ccagaacgac aaacaaaagg    9840
ctatcaacta tctgatgcaa tttgcacaca aggtatcggg gaaataccgt ggtgtggcaa    9900
agcttgaagg aaatactaag gcaaaggtac tgcaagtgct cgcaacattc gcttatgcgg    9960
attattgccg tagtgccgcg acgccggggg caagatgcag agattgccat ggtacaggcc    10020
gtgcggttga tattgccaaa acagagctgt gggggagagt tgtcgagaaa gagtgcggaa    10080
gatgcaaagg cgtcggctat tcaaggatgc cagcaagcgc agcatatcgc gctgtgacga    10140
tgctaatccc aaaccttacc caacccacct ggtcacgcac tgttaagccg ctgtatgacg    10200
```

-continued

```
ctctggtggt gcaatgccac aaagaagagt caatcgcaga caacattttg aatgcggtca    10260
cacgttagca gcatgattgc cacggatggc aacatattaa cggcatgata ttgacttatt    10320
gaataaaatt gggtaaattt gactcaacga tgggttaatt cgctcgttgt ggtagtgaga    10380
tgaaaagagg cggcgcttac taccgattcc gcctagttgg tcacttcgac gtatcgtctg    10440
gaactccaac catcgcaggc agagaggtct gcaaaatgca atcccgaaac agttcgcagg    10500
taatagttag agcctgcata acggtttcgg gattttttat atctgcacaa caggtaagag    10560
cattgagtcg ataatcgtga agagtcggcg agcctggtta gccagtgctc tttccgttgt    10620
gctgaattaa gcgaataccg gaagcagaac cggatcacca aatgcgtaca ggcgtcatcg    10680
ccgcccagca acagcacaac ccaaactgag ccgtagccac tgtctgtcct gaattcatta    10740
gtaatagtta cgctgcggcc ttttacacat gaccttcgtg aaagcgggtg gcaggaggtc    10800
gcgctaacaa cctcctgccg ttttgcccgt gcatatcggt cacgaacaaa tctgattact    10860
aaacacagta gcctggattt gttctatcag taatcgacct tattcctaat taaatagagc    10920
aaatcccctt attggggta agacatgaag atgccagaaa acatgacct gttggccgcc    10980 attctcgcgg caaaggaaca aggcatcggg gcaatccttg cgtttgcaat ggcgtacctt    11040
cgcggcagat ataatggcgg tgcgtttaca aaaacagtaa tcgacgcaac gatgtgcgcc    11100
attatcgcct ggttcattcg tgaccttctc gacttcgccg gactaagtag caatctcgct    11160
tatataacga gcgtgtttat cggctacatc ggtactgact cgattggttc gcttatcaaa    11220
cgcttcgctg ctaaaaaagc cggagtagaa gatggtagaa atcaataatc aacgtaaggc    11280
gttcctcgat atgctggcgt ggtcggaggg aactgataac ggacgtcaga aaaccagaaa    11340
tcatggttat gacgtcattg taggcggaga gctatttact gattactccg atcaccctcg    11400
caaacttgtc acgctaaacc caaaactcaa atcaacaggc gcttaagact ggccgtcgtt    11460
ttacaacaca gaaagagttt gtagaaacgc aaaaaggcca tccgtcaggg gccttctgct    11520
tagtttgatg cctggcagtt ccctactctc gccttccgct tcctcgctca ctgactcgct    11580
gcgctcggtc gttcggctgc ggcgagcggt atcagctcac tcaaaggcgg taatacggtt    11640
atccacagaa tcaggggata acgcaggaaa gaacatgtga gcaaaaggcc agcaaaaggc    11700
caggaaccgt aaaaaggccg cgttgctggc gtttttccat aggctccgcc ccctgacga    11760 gcatcacaaa aatcgacgct caagtcagag gtggcgaaac ccgacaggac tataaagata    11820
ccaggcgttt cccctggaa gctccctcgt gcgctctcct gttccgaccc tgccgcttac    11880
cggatacctg tccgcctttc tcccttcggg aagcgtggcg ctttctcata gctcacgctg    11940
taggtatctc agttcggtgt aggtcgttcg ctccaagctg ggctgtgtgc acgaaccccc    12000
cgttcagccc gaccgctgcg ccttatccgg taactatcgt cttgagtcca acccggtaag    12060
acacgactta tcgccactgg cagcagccac tggtaacagg attagcagag cgaggtatgt    12120
aggcggtgct acagagttct tgaagtggtg gcctaactac ggctacacta agaacagt    12180 atttggtatc tgcgctctgc tgaagccagt taccttcgga aaaagagttg gtagctcttg    12240
atccggcaaa caaccaccg ctggtagcgg tggttttttt gtttgcaagc agcagattac    12300
gcgcagaaaa aaaggatctc aagaagatcc tttgatcttt tctacggggt ctgacgctca    12360
gtggaacgac gcgcgcgtaa ctcacgttaa gggattttgg tcatgagctt cgccgtccc    12420 gtcaagtcag cgtaatgctc tgcttt                                         12446
```